(12) United States Patent
Ono

(10) Patent No.: US 10,113,154 B2
(45) Date of Patent: Oct. 30, 2018

(54) METHOD FOR PRODUCING STEVIOL GLYCOSIDE

(71) Applicant: SUNTORY HOLDINGS LIMITED, Osaka (JP)

(72) Inventor: Eiichiro Ono, Osaka (JP)

(73) Assignee: SUNTORY HOLDINGS LIMITED, Osaka (JP)

(*) Notice: Subject to any disclaimer, the term of this patent is extended or adjusted under 35 U.S.C. 154(b) by 904 days.

(21) Appl. No.: 14/386,934

(22) PCT Filed: Mar. 14, 2013

(86) PCT No.: PCT/JP2013/058188
§ 371 (c)(1),
(2) Date: Sep. 22, 2014

(87) PCT Pub. No.: WO2013/146555
PCT Pub. Date: Oct. 3, 2013

(65) Prior Publication Data
US 2015/0128306 A1 May 7, 2015

(30) Foreign Application Priority Data

Mar. 27, 2012 (JP) ................................. 2012-071959

(51) Int. Cl.
| | |
|---|---|
| *C12N 9/10* | (2006.01) |
| *C07K 14/415* | (2006.01) |
| *C12P 19/44* | (2006.01) |
| *A61K 8/60* | (2006.01) |
| *C12P 19/56* | (2006.01) |
| *C07H 15/256* | (2006.01) |
| *A61Q 19/00* | (2006.01) |
| *A23L 27/30* | (2016.01) |

(52) U.S. Cl.
CPC ............ *C12N 9/1048* (2013.01); *A61K 8/602* (2013.01); *C07K 14/415* (2013.01); *C12N 9/10* (2013.01); *C12P 19/44* (2013.01); *C12P 19/56* (2013.01); *C12Y 204/01* (2013.01); *A23L 27/36* (2016.08); *A23V 2250/262* (2013.01); *A61K 2800/10* (2013.01); *A61Q 19/00* (2013.01); *C07H 15/256* (2013.01)

(58) Field of Classification Search
CPC ...... C12P 19/44; A23V 2250/262; A23L 2/60; C12N 9/1051; C12N 15/52; C12N 9/1048; C12Y 204/01001
See application file for complete search history.

(56) References Cited

U.S. PATENT DOCUMENTS

| | | | |
|---|---|---|---|
| 4,219,571 A | 8/1980 | Miyake | |
| 4,590,160 A | 5/1986 | Nishihashi et al. | |
| 4,892,938 A * | 1/1990 | Giovanetto | ............ A61K 36/28 |
| | | | 536/127 |
| 6,982,077 B2 * | 1/2006 | Hammer | .................. A61K 8/26 |
| | | | 424/401 |
| 9,243,273 B2 | 1/2016 | Markosyan et al. | |
| 9,562,251 B2 | 2/2017 | Kishore et al. | |
| 2008/0064063 A1 | 3/2008 | Brandle et al. | |
| 2010/0316782 A1 | 12/2010 | Shi et al. | |
| 2014/0017378 A1 | 1/2014 | Purkayastha et al. | |
| 2014/0030381 A1 | 1/2014 | Markysyan | |
| 2014/0357588 A1 | 12/2014 | Markosyan et al. | |
| 2016/0186225 A1 | 6/2016 | Mikkelsen et al. | |

FOREIGN PATENT DOCUMENTS

| | | | |
|---|---|---|---|
| EP | 1 897 951 | 12/2010 | |
| EP | 2826861 | 1/2015 | |
| JP | 5-255372 | 10/1993 | |
| WO | 2011/153378 | 12/2011 | |
| WO | WO 2011/153378 A1 * | 12/2011 | ............... A01H 5/00 |
| WO | 2013/022989 | 2/2013 | |
| WO | 2013/176738 | 11/2013 | |

OTHER PUBLICATIONS

Richman, Alex, et al. "Functional genomics uncovers three glucosyltransferases involved in the synthesis of the major sweet glucosides of Stevia rebaudiana." The Plant Journal 41.1 (2005): 56-67.*
Brandle, J. E., and P. G. Telmer. "Steviol glycoside biosynthesis." Phytochemistry 68.14 (2007): 1855-1863.*
Ceunen, Stijn, and Jan MC Geuns. "Steviol glycosides: chemical diversity, metabolism, and function." Journal of natural products 76.6 (2013): 1201-1228.*
Osmani, Sarah A., Søren Bak, and Birger Lindberg Møller. "Substrate specificity of plant UDP-dependent glycosyltransferases predicted from crystal structures and homology modeling." Phytochemistry 70.3 (2009): 325-347.*
Kinghorn, A. Douglas, ed. Stevia: the genus *Stevia*. CRC Press, 2003 (Year: 2003).*
Richman, Alex, et al. "Functional genomics uncovers three glucosyltransferases involved in the synthesis of the major sweet glucosides of Stevia rebaudiana." The Plant Journal 41.1 (2005): 56-67. (Year: 2005).*
Richman A., Swanson A., Humphrey T., Chapman R., McGarvey B., Pocs R., Brandle J.; "Functional genomics uncovers three glucosyltransferases involved in the synthesis of the major sweet glucosides of Stevia rebaudiana."; Plant J. 41:56-67(2005). (Year: 2005).*
Kasai et al., "Stevia-ha no Kanmi Diterpene Haitotai-Rebaudioside-A, -D, -E Oyobi Kanren Haitotai no Gosei Narabini Kanmi to Kagaku Kozo tono Sokan-", *Journal of the Chemical Society of Japan*, No. 5, pp. 726-735 (1981), including English language Abstract.

(Continued)

*Primary Examiner* — Lee A Visone
*Assistant Examiner* — Weihua Fan
(74) *Attorney, Agent, or Firm* — Greenblum & Bernstein, P.L.C.

(57) ABSTRACT

The invention provides a method for producing steviol glycosides. The invention provides a transformant having introduced therein the steviol glucosyltransferase and a method for producing steviol glycosides using the transformant.

18 Claims, 5 Drawing Sheets
Specification includes a Sequence Listing.

(56) References Cited

OTHER PUBLICATIONS

Richman et al., "Functional genomics uncovers three glucosyltransferases involved in the synthesis of the major sweet glucosides of Stevia rebaudiana ", *Plant J.*, vol. 41, No. 1 , 2005, pp. 56-67 (2005).
Brandle et al., "Steviol glycoside biosynthesis", *Phytochemistry*, vol. 68, No. 14, pp. 1855-1863 (2007).
Mohamed et al., "UDP-dependent glycosyltranferases involved in the biosynthesis of steviol glycosides ", *J. Plant Physiol.*, vol. 168, No. 10, pp. 1136-1141 (2011).
Mizutani et al., "Diversification of P450 genes during land plant evolution", *Annu. Rev. Plant Biol.*, vol. 61, pp. 291-315 (2010).
Madhav et al., "Functional and structural variation of uridine diphosphate glycosyltransferase (UGT) gene of *Stevia rebaudina*-UGTr involved in the synthesis of rebaudioside A", *Plant Physiol. Biochem.*, vol. 63, pp. 245-253 published online Dec. 17, 2012.
U.S. Appl. No. 14/402,165 to Eiichiro Ono, filed Nov. 19, 2014.
U.S. Appl. No. 14/383,698 to Eiichiro Ono et al., filed Sep. 8, 2014.
International Search Report for PCT/JP2013/058188, dated Apr. 23, 2013.
Tanaka, "Improvement of taste of natural sweeteners", *Pure & Appl. Chem.*, vol. 69, No. 4, pp. 675-683 (1997).
Extended European Search Report issued in EP Patent Application No. 13769588.8, dated Oct. 2, 2015.

\* cited by examiner

Figure 1

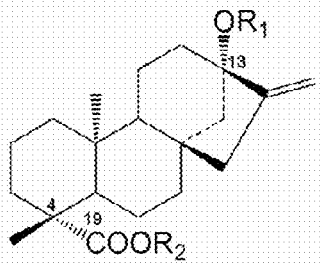

| Name | R₁ | R₂ |
|---|---|---|
| Steviol | H | H |
| Steviolmonoside | Glc | H |
| Steviolbioside | Glc-Glc(β2→1) | H |
| Dulcoside A | Glc-Rha(β2→1) | H |
| Rubusoside | Glc | Glc |
| Stevioside | Glc-Glc(β2→1) | Glc |
| Rebaudioside A | Glc-Glc(β2→1)<br>\|<br>Glc(β3→1) | Glc |
| Rebaudioside B | Glc-Glc(β2→1)<br>\|<br>Glc(β3→1) | H |
| Rebaudioside C (Dulcoside B) | Glc-Rha(β2→1)<br>\|<br>Glc(β3→1) | Glc |
| Rebaudioside D | Glc-Glc(β2→1)<br>\|<br>Glc(β3→1) | Glc-Glc(β2→1) |
| Rebaudioside E | Glc-Glc(β2→1) | Glc-Glc(β2→1) |
| Rebaudioside F | Glc-Xyl(β2→1)<br>\|<br>Glc(β3→1) | Glc |

METHOD FOR PRODUCING STEVIOL GLYCOSIDE

SEQUENCE LISTING

The instant application contains a Sequence Listing which has been submitted electronically in ASCII format and is hereby incorporated by reference in its entirety. Said ASCII copy, created on Dec. 8, 2014, is named P46223_SL.txt and is 23,624 bytes in size.

TECHNICAL FIELD

The present invention relates to a method for producing steviol glycosides, a transformant highly expressing steviol glucosyltransferases, steviol glycosides produced by the method and use thereof.

RELATED ART

The leaves of *Stevia rebaudiana* contain a secondary metabolite called steviol, which is a member of diterpenoids. Steviol glycosides elicit a sweet taste that are up to about 300 times the sweetness of sugar, and have been used as non-caloric sweeteners in the food industry. Obesity is globally increasing as a serious social problem, and demand for non-caloric sweeteners is growing every day from viewpoints of promoting health and reducing medical expenses. Currently, Aspartame and Acesulfame Potassium, which are artificially synthesized amino acid derivatives, are used as artificial sweeteners. However, it is expected that naturally occurring non-caloric sweeteners like steviol glycosides are more likely to enjoy public acceptance.

Steviol contained in the leaves of *stevia* is modified with sugars finally to a glycoside called rebaudioside A with four glucose moieties attached (FIG. 1). Its precursor steviol triglycoside, stevioside, is most abundant quantitatively, and rebaudioside A and stevioside are the main components of sweetness in *stevia*. In addition to them, the presence of glycosides considered to be reaction intermediates and analogs with different sugars are known.

Enzyme genes encoding biosynthesis of rebaudioside A have been isolated through an expressed sequence tag (EST) analysis of *stevia* (Non-Patent Documents 1 and 2, Patent Document 1). Steviol is produced through hydroxylation at position 13 of ent-kaurenoic acid, i.e., a precursor of plant hormone diterpenoid, gibberellins, by cytochrome P450 enzyme ent-kaurenoic acid, 13-hydroxylase (EK13H) (FIG. 2) (Non-Patent Document 3, Patent Document 1). The 13-hydroxy group of steviol is first glycosylated (monoglucosylation) by UGT85C2 to produce steviolmonoside. The position 2 of the glucose at position 13 of steviolmonoside is further glucosylated to form steviolbioside, or the carboxyl group at position 19 of steviolmonoside is glucosylated to form a steviol diglycoside called rubusoside. Steviolbioside or rubusoside thus produced is considered to undergo further glycosylation to form steviol glycosides such as stevioside and rebaudioside A. UGT74G1 and UGT76G1 are known as enzyme genes involved in formation of steviol glycosides.

UGT74G1 is known to catalyze glucosylation of the position 19 of steviolmonoside (Non-Patent Document 1). UGT74G1 also catalyzes glucosylation of steviolbioside to produce stevioside which is a steviol triglycoside. The content of stevioside is most abundant in the leaves of *stevia*; stevioside is known to be approximately 250 to 300 times sweeter than sugar. This stevioside is further glucosylated by UGT76G1 to produce steviol tetraglycoside, rebaudioside A, which is the sweetest (350 to 450 times sweeter than sugar) and reportedly has a favorable quality of taste.

In the previous study (Non-Patent Document 2), several types of glucosyltransferases (UGT) are reported by the EST analysis of *stevia* leaves. However, detailed enzyme activities of all these enzymes have not been fully investigated.

PRIOR ART DOCUMENTS

Patent Document

[Patent Document 1] EP 1 897 951 B1

Non-Patent Documents

[Non-Patent Document 1] Brandle and Telmer (2007) Phytochemistry 68, 1855-1863
[Non-Patent Document 2] Richman et al (2005) Plant J. 41, 56-67
[Non-Patent Document 3] Mizutani and Ohta (2010) Annu. Rev. Plant Biol. 61, 291-315

DISCLOSURE OF THE INVENTION

Problems to be Solved by the Invention

As a result of extensive studies, the present inventors have succeeded in enzymes that catalyze glycosylation of the glucose at position 19 of steviol glycosides in *stevia* and gene sequences encoding the enzymes. The present invention is based on the above finding.

Means for Solving the Problem

That is, the present invention is described as follows.

[1] A method for producing a steviol glycoside, which comprises the step of reacting a protein according to any one selected from the group consisting of (a) to (c) below with a UDP-sugar and a compound represented by general formula (I) below:

(a) a protein consisting of the amino acid sequence of SEQ ID NO: 2;

(b) a protein consisting of an amino acid sequence wherein 1 to 48 amino acids are deleted, substituted, inserted and/or added in the amino acid sequence of SEQ ID NO: 2, and having an activity of adding a sugar molecule to the carboxyl at position 19 of a compound represented by general formula (I) below; and, (c) a protein having an amino acid sequence having at least 90% sequence identity with the amino acid sequence of SEQ ID NO: 2, and having an activity of adding a sugar molecule to the carboxyl at position 19 of a compound represented by general formula (I) below:

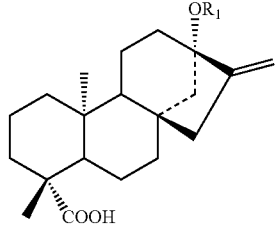

(I)

wherein, $R_1$ represents H, a $C_1$-$C_{20}$ alkyl, a $C_2$-$C_{20}$ alkenyl, a $C_2$-$C_{20}$ alkynyl, a $C_4$-$C_{20}$ alkyldienyl, a $C_6$-$C_{18}$ aryl, a $C_6$-$C_{20}$ alkylaryl, a $C_6$-$C_{20}$ arylalkyl, a $C_4$-$C_{20}$ cycloalkyl, a $C_4$-$C_{20}$ cycloalkenyl, a ($C_3$-$C_{10}$ cycloalkyl) $C_1$-$C_{10}$ alkyl, or a sugar residue.

[2] The method according to [1] above, wherein said sugar in the UDP-sugar is a hexose.

[3] The method according to [1] above, wherein said sugar in the UDP-sugar is one selected from the group consisting of glucose, mannose and galactose.

[4] The method according to [1] above, wherein said sugar added to the carboxyl at position 19 is a hexose.

[5] The method according to [1] above, wherein said sugar added to the carboxyl at position 19 is one selected from the group consisting of glucose, mannose and galactose.

[6] The method according to [1] above, wherein said $R_1$ is H or the sugar residue which is a glucose monomer, glucose dimer or glucose trimer.

[7] The method according to [1] above, wherein said compound is steviolmonoside, steviolbioside or steviol.

[8] The method according to [1] above, wherein said steviol glycoside is steviolbioside, stevioside, rebaudioside A, rebaudioside B, rebaudioside C, rebaudioside D, rebaudioside E, rebaudioside F, or a combination thereof.

[9] A non-human transformant, into which a polynucleotide selected from the group consisting of (a) to (e) below is introduced:

(a) a polynucleotide comprising the nucleotide sequence of SEQ ID NO: 1;

(b) a polynucleotide encoding a protein consisting of the amino acid sequence of SEQ ID NO: 2;

(c) a polynucleotide encoding a protein consisting of an amino acid sequence wherein 1 to 48 amino acids are deleted, substituted, inserted and/or added in the amino acid sequence of SEQ ID NO: 2, and having an activity of adding a sugar molecule to the carboxyl at position 19 of a compound represented by general formula (I) below;

(d) a polynucleotide encoding a protein having an amino acid sequence having at least 90% sequence identity with the amino acid sequence of SEQ ID NO: 2, and having an activity of adding a sugar molecule to the carboxyl at position 19 of a compound represented by general formula (I) below; and, (e) a polynucleotide that hybridizes under highly stringent conditions with a polynucleotide consisting of a nucleotide sequence complementary to the nucleotide sequence of SEQ ID NO: 1 and encodes a protein having an activity of adding a sugar molecule to the carboxyl at position 19 of a compound represented by general formula (I) below:

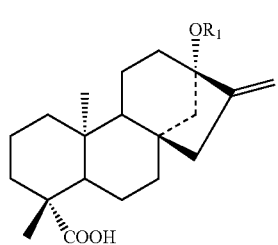

(I)

wherein, $R_1$ represents H, a $C_1$-$C_{20}$ alkyl, a $C_2$-$C_{20}$ alkenyl, a $C_2$-$C_{20}$ alkynyl, a $C_4$-$C_{20}$ alkyldienyl, a $C_6$-$C_{18}$ aryl, a $C_6$-$C_{20}$ alkylaryl, a $C_6$-$C_{20}$ arylalkyl, a $C_4$-$C_{20}$ cycloalkyl, a $C_4$-$C_{20}$ cycloalkenyl, a ($C_3$-$C_{10}$ cycloalkyl) $C_1$-$C_{10}$ alkyl, or a sugar residue.

[10] The transformant according to [9] above, wherein said sugar molecule is a hexose.

[11] The transformant according to [9] above, wherein said sugar molecule is one selected from the group consisting of glucose, mannose and galactose.

[12] The transformant according to [9] above, wherein said $R_1$ is H or the sugar residue which is a glucose monomer, glucose dimer or glucose trimer.

[13] The transformant according to [9] above, wherein said compound is steviolmonoside, steviolbioside or steviol.

[14] The transformant according to [9] above, wherein said polynucleotide is inserted into an expression vector.

[15] The transformant according to [9] above, which is a plant.

[16] An extract from the transformant according to [9] above.

[17] A food, pharmaceutical composition or industrial material comprising the extract according to [16] above.

[18] A method for producing a steviol glycoside, which comprises using the non-human transformant according to [9] above.

[19] The method according to [18] above, wherein said steviol glycoside is steviolbioside, stevioside, rebaudioside A, rebaudioside B, rebaudioside C, rebaudioside D, rebaudioside E, rebaudioside F, or a combination thereof.

[20] A protein consisting of the amino acid sequence of SEQ ID NO: 2.

[21] A polynucleotide encoding a protein consisting of the amino acid sequence of SEQ ID NO: 2.

[22] The polynucleotide according to [21] above consisting of the nucleotide sequence of SEQ ID NO: 1.

Effects of the Invention

According to the method of the present invention, steviol glycosides (e.g., rubusoside, stevioside, rebaudioside A, etc.) can be produced with a high efficiency. The transformants of the present invention have a high content of steviol glycosides (e.g., rubusoside, stevioside, rebaudioside A, etc.). Accordingly, steviol glycosides (e.g., rubusoside, stevioside, rebaudioside A, etc.) can be efficiently extracted and purified from these transformants.

BRIEF DESCRIPTION OF DRAWINGS

FIG. 1 shows the names and structures of steviol glycosides. In FIG. 1, "Glc-Glc (β2→1)" denotes that "Glc-Glc" binds through β2,1 glycoside bond, and "Glc-Glc (β3→1)" denotes that "Glc-Glc" binds through β3,1 glycoside bond.

Figure 2:
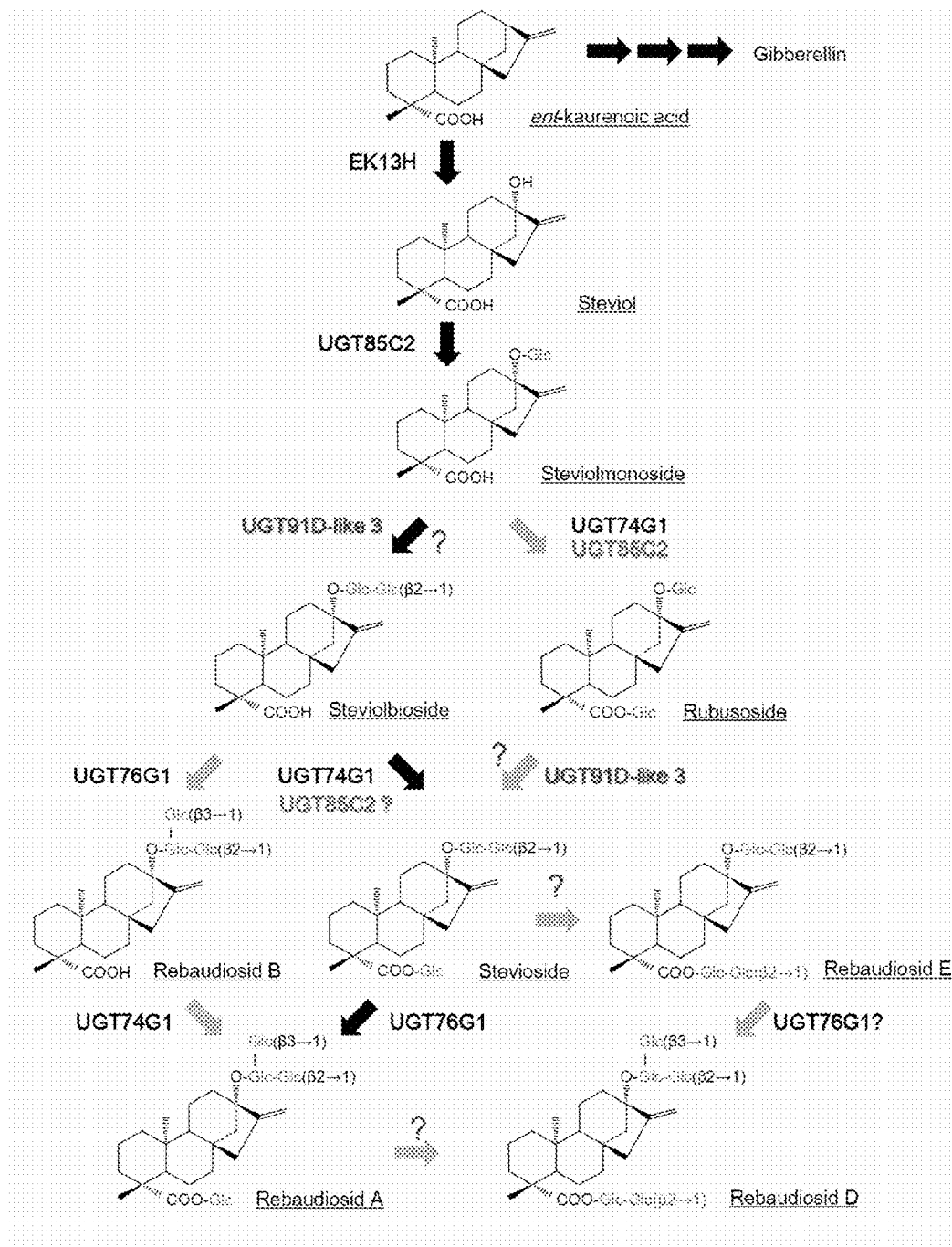
FIG. 2 shows presumed biosynthetic pathway of steviol glycosides.
Figure 3:
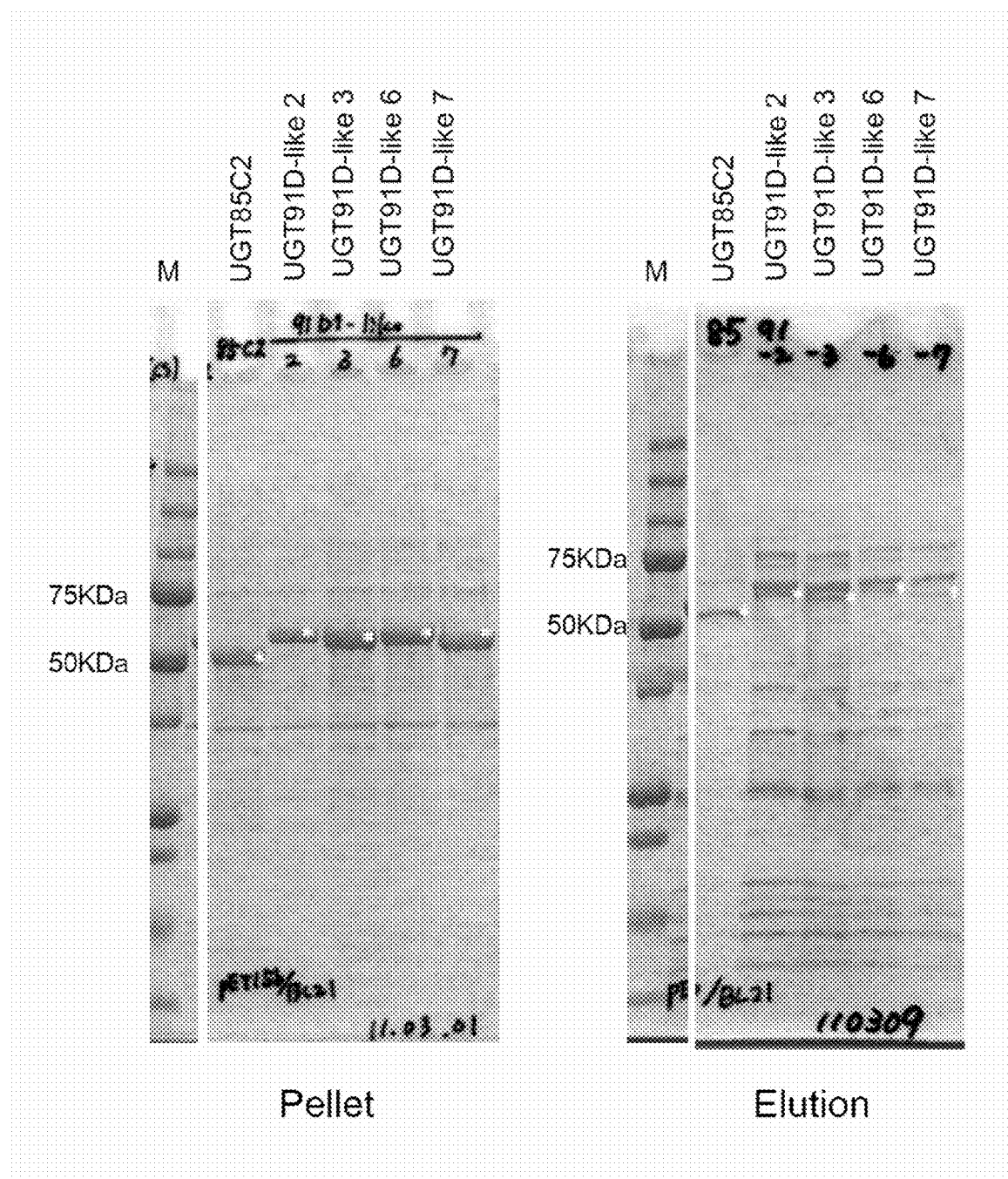
FIG. 3 shows the SDS-PAGE results of *stevia* UGT protein expressed in *Escherichia coli*. The CBB stain patterns of the pellet fraction and the eluted fraction with imidazole solution are shown in the left side and the right side, respectively. Asterisk denotes the expressed recombinant protein.

Hereinafter, the present invention is described in detail. The embodiments described below are presented by way of example merely to describe the invention but not limited only to the following embodiments. The present invention may be implemented in various ways without departing from the gist of the invention.

All of the publications, published patent applications, patents and other patent documents cited in the specification are herein incorporated by reference in their entirety. The specification hereby incorporates by reference the contents of the specification and drawings in Japanese Patent Application (No. 2012-071959) filed Mar. 27, 2012, from which the priority was claimed.

The present inventors have elucidated for the first time that the enzyme protein responsible for glycosylation to the glucose at C19-position in steviol glycosides is UGT85C2.

The CDS sequence and amino acid sequence of UGT85C2 are SEQ ID NOS: 1 and 2, respectively. The polynucleotides and enzyme described above may be obtained by the methods described in EXAMPLES later described, known genetic engineering techniques, known methods for synthesis, and so on.

1. Method for Producing Steviol Glycosides

The present invention provides a method for producing steviol glycosides, which comprises the step of reacting a protein according to any one selected from the group consisting of (a) to (c) below (hereinafter referred to as "the protein of the present invention") with a UDP-sugar and a compound represented by general formula (I) below:

(a) a protein consisting of the amino acid sequence of SEQ ID NO: 2;

(b) a protein consisting of an amino acid sequence wherein 1 to 48 amino acids are deleted, substituted, inserted and/or added in the amino acid sequence of SEQ ID NO: 2, and having an activity of adding a sugar molecule to the carboxyl at position 19 of a compound represented by general formula (I) below; and, (c) a protein having an amino acid sequence having at least 90% sequence identity with the amino acid sequence of SEQ ID NO: 2, and having an activity of adding a sugar molecule to the carboxyl at position 19 of a compound represented by general formula (I) below:

79, 6409 (1982)," "Gene, 34, 315 (1985)," "Nuc. Acids. Res., 13, 4431 (1985)," "Proc. Natl. Acad. Sci. USA, 82, 488 (1985)," etc.

As used herein, "the protein consisting of an amino acid sequence wherein 1 to 48 amino acids are deleted, substituted, inserted and/or added in the amino acid sequence of SEQ ID NO: 2, and having an activity of adding a sugar molecule to the carboxyl at position 19 of a compound represented by general formula (I)" includes proteins containing an amino acid sequence wherein, e.g., 1 to 48, 1 to 47, 1 to 46, 1 to 45, 1 to 44, 1 to 43, 1 to 42, 1 to 41, 1 to 40, 1 to 39, 1 to 38, 1 to 37, 1 to 36, 1 to 35, 1 to 34, 1 to 33, 1 to 32, 1 to 31, 1 to 30, 1 to 29, 1 to 28, 1 to 27, 1 to 26, 1 to 25, 1 to 24, 1 to 23, 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9 (1 to several), 1 to 8, 1 to 7, 1 to 6, 1 to 5, 1 to 4, 1 to 3, 1 to 2, or one amino acid is/are deleted, substituted, inserted and/or added in the amino acid sequence of SEQ ID NO: 2, and having the activity of adding a sugar molecule to the carboxyl at position 19 of the compound represented by general formula (I). In general, the number of deletions, substitutions, insertions, and/or additions is preferably smaller.

Such proteins include proteins having an amino acid sequence having the identity of approximately 90% or higher, 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher, or 99.9% or higher, with the amino acid sequence of SEQ ID NO: 2, and having the activity of adding a sugar molecule to the carboxyl at position 19 of the compound represented by general formula (I). As the identity percentage described above is higher, the protein is preferred in general.

As used herein, "the activity of adding a sugar molecule to the carboxyl at position 19 of the compound represented by general formula (I)" is intended to mean the activity of adding sugars to the carboxyl group at position 19 of the compound represented by general formula (I) below.

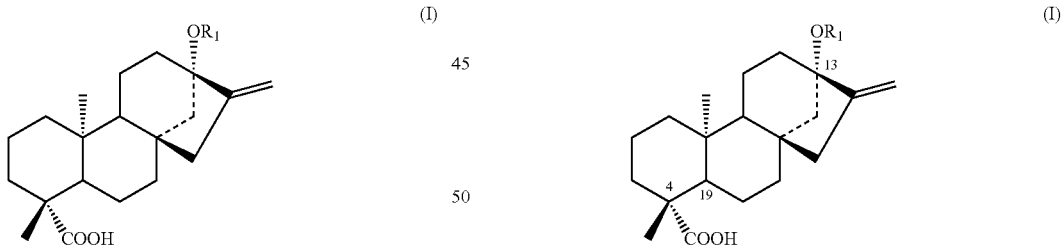

wherein, $R_1$ represents H, a $C_1$-$C_{20}$ alkyl, a $C_2$-$C_{20}$ alkenyl, a $C_2$-$C_{20}$ alkynyl, a $C_4$-$C_{20}$ alkyldienyl, a $C_6$-$C_{18}$ aryl, a $C_6$-$C_{20}$ alkylaryl, a $C_6$-$C_{20}$ arylalkyl, a $C_4$-$C_{20}$ cycloalkyl, a $C_4$-$C_{20}$ cycloalkenyl, a ($C_3$-$C_{10}$ cycloalkyl) $C_1$-$C_{10}$ alkyl, or a sugar residue.

The proteins described in (b) or (c) above are typically mutants of the naturally occurring polypeptide of SEQ ID NO: 2 and also include those proteins which may be artificially obtained using site-directed mutagenesis described in, e.g., "Sambrook & Russell, Molecular Cloning: A Laboratory Manual Vol. 3, Cold Spring Harbor Laboratory Press 2001," "Ausubel, Current Protocols in Molecular Biology, John Wiley & Sons 1987-1997," "Nuc. Acids. Res., 10, 6487 (1982)," "Proc. Natl. Acad. Sci. USA, In general formula (I), $R_1$ represents H, a $C_1$-$C_{20}$ alkyl, a $C_2$-$C_{20}$ alkenyl, a $C_2$-$C_{20}$ alkynyl, a $C_4$-$C_{20}$ alkyldienyl, a $C_6$-$C_{18}$ aryl, a $C_6$-$C_{20}$ alkylaryl, a $C_6$-$C_{20}$ arylalkyl, a $C_4$-$C_{20}$ cycloalkyl, a $C_4$-$C_{20}$ cycloalkenyl, a ($C_3$-$C_{10}$ cycloalkyl) $C_1$-$C_{10}$ alkyl, or a sugar residue.

As used herein, the "$C_1$-$C_{20}$ alkyl" is preferably a $C_1$-$C_{10}$ alkyl, and more preferably a $C_1$-$C_6$ alkyl. The alkyl group includes, but not limited to, methyl, ethyl, propyl, isopropyl, n-butyl, sec-butyl, tert-butyl, pentyl, hexyl, dodecanyl, etc.

As used herein, the "$C_2$-$C_{20}$ alkenyl" is preferably a $C_2$-$C_{10}$ alkenyl, and more preferably a $C_2$-$C_6$ alkenyl. The alkenyl group includes, but not limited to, vinyl, allyl, propenyl, isopropenyl, 2-methyl-1-propenyl, 2-methylallyl, 2-butenyl, etc.

As used herein, the "$C_2$-$C_{20}$ alkynyl" is preferably a $C_2$-$C_{10}$ alkynyl, and more preferably a $C_2$-$C_6$ alkynyl. The alkynyl group includes, but not limited to, ethynyl, 2-propynyl, 2-butynyl, etc.

As used herein, the "$C_4$-$C_{20}$ alkyldienyl" is preferably a $C_4$-$C_{10}$ alkyldienyl, and more preferably a $C_4$-$C_6$ alkyldienyl. The alkyldienyl group includes, but not limited to, 1,3-butadienyl, etc.

As used herein, the "$C_6$-$C_{18}$ aryl" is preferably a $C_6$-$C_{10}$ aryl. The aryl group includes, but not limited to, phenyl, 1-naphthyl, 2-naphthyl, indenyl, biphenylyl, anthryl, phenanthryl, etc.

As used herein, the "$C_6$-$C_{20}$ alkylaryl" is preferably a $C_6$-$C_{12}$ alkylaryl. The alkylaryl group includes, but not limited to, o-tolyl, m-tolyl, p-tolyl, 2,3-xylyl, 2,4-xylyl, 2,5-xylyl, o-cumenyl, m-cumenyl, p-cumenyl, mesityl, etc.

As used herein, the "$C_6$-$C_{20}$ arylalkyl" is preferably a $C_6$-$C_{12}$ arylalkyl. The arylalkyl group includes, but not limited to, benzyl, phenethyl, diphenylmethyl, triphenylmethyl, 1-naphthylmethyl, 2-naphthylmethyl, 2,2-diphenylethyl, 3-phenylpropyl, 4-phenylbutyl, 5-phenylpentyl, etc.

As used herein, the "$C_4$-$C_{20}$ cycloalkyl" is preferably a $C_4$-$C_{10}$ cycloalkyl. The cycloalkyl group includes, but not limited to, cyclopropyl, cyclobutyl, cyclopentyl, cyclohexyl, etc.

As used herein, the "$C_4$-$C_{20}$ cycloalkenyl" is preferably a $C_4$-$C_{10}$ cycloalkenyl. The cycloalkenyl group includes, but not limited to, cyclopropenyl, cyclobutenyl, 2-cyclopenten-1-yl, 2-cyclohexen-1-yl, 3-cyclohexen-1-yl, etc.

As used herein, examples of the "($C_3$-$C_{10}$ cycloalkyl) $C_1$-$C_{10}$ alkyl" include methylcyclopropyl, ethylcyclopropyl, methylcyclobutyl, ethylcyclopentyl, methylcyclohexyl, etc.

As used herein, the "sugar residue" may include, but not limited to, a residue of one or more sugars including a pentose, a hexose or a combination thereof (excluding xylose, rhamnose or a combination thereof).

Examples of the pentose include ribose, arabinose and lyxose, and examples of the hexose include allose, altrose, glucose, mannose, gulose, idose, galactose and talose.

Preferably, the "sugar residue" refers to a residue of sugar consisting of at least one hexose unit, and more preferably, a residue from a glucose monomer (-Glc), glucose dimer (-Glc-Glc) or glucose trimer (-Glc(Glc)-Glc). In the sugar residue from the glucose dimer, glucose is linked to each other preferably through a β2,1 glycoside bond. In the sugar residue from the glucose trimer, glucose is linked to each other preferably through a β2,1 glycoside bond and a β3,1 glycoside bond.

The compound of general formula (I) is preferably steviolmonoside, steviolbioside or steviol.

The sugar molecule added by the protein of the present invention to the carboxyl at position 19 of the compound represented by general formula (I) may include, but not limited to, sugar molecules consisting of at least one pentose, hexose or a combination thereof (excluding xylose, rhamnose or a combination thereof). Examples of the pentose and hexose are the same as described above. The sugar molecule described above is preferably a hexose, and more preferably, a hexose selected from the group consisting of glucose, mannose and galactose. The sugar molecule above is most preferably glucose.

The activity of adding the sugar molecule to the carboxyl at position 19 of the compound represented by general formula (I) can be confirmed as follows. After incubation in a buffer (e.g., sodium phosphate buffer or potassium phosphate buffer) in the neutral region of pH 6.0-8.0, which contains 1-500 ng (preferably, 50-200 ng, most preferably, 100 ng) of a test protein, 1-1000 μM (preferably, 100-700 μM, most preferably, 500 μM) of UDP sugar (e.g., UDP-glucose) and 1-500 μM (preferably, 100-500 μM, most preferably, 250 μM) of a substrate compound (compound of general formula (I)) at a temperature of 20-40° C. for 10 minutes to 2 hours, the substrate compound above is purified and the monoterpene purified is analyzed by known means such as the LC-MS analysis (Liquid Chromatography-Mass Spectrometry), etc.

In the case that the sugar molecule attached to the carboxyl at position 19 of the compound represented by general formula (I) is detected as a result of the LC-MS analysis, the test protein described above is considered to have the activity of adding the sugar molecule to the carboxyl at position 19 of the compound represented by general formula (I).

In general, the glycosylation reaction is completed approximately in a minute to 12 hours.

The deletion, substitution, insertion and/or addition of one or more amino acid residues in an amino acid sequence of the protein of the invention is intended mean that one or a plurality of amino acid residues are deleted, substituted, inserted and/or added at one or a plurality of positions in the same amino acid sequence. Two or more types of deletions, substitutions, insertions and additions may occur at the same time.

Examples of the amino acid residues which are mutually substitutable are given below. Amino acid residues in the same group are mutually substitutable. Group A: leucine, isoleucine, norleucine, valine, norvaline, alanine, 2-aminobutanoic acid, methionine, o-methylserine, t-butylglycine, t-butylalanine and cyclohexylalanine; Group B: aspartic acid, glutamic acid, isoaspartic acid, isoglutamic acid, 2-aminoadipic acid and 2-aminosuberic acid; Group C: asparagine and glutamine; Group D: lysine, arginine, ornithine, 2,4-diaminobutanoic acid and 2,3-diaminopropionic acid; Group E: proline, 3-hydroxyproline and 4-hydroxyproline; Group F: serine, threonine and homoserine; and Group G: phenylalanine and tyrosine.

The protein of the present invention may be obtained by expressing a polynucleotide (cf., "the polynucleotide of the present invention" later described) encoding the protein in an appropriate host cell. The protein may also be produced by chemical synthesis methods such as the Fmoc method (fluorenylmethyloxycarbonyl method), the tBoc method (t-butyloxycarbonyl method), etc. In addition, peptide synthesizers available from Advanced Automation Peptide Protein Technologies, Perkin Elmer, Protein Technology Instrument, PerSeptive, Applied Biosystems, SHIMADZU Corp., etc. may also be used for the chemical synthesis.

As used herein, the term "UDP-sugar" refers to uridine diphosphate (Uridine DiPhosphate: UDP)-bound sugar. In the UDP-sugar, preferred examples of the sugar moiety include sugars composed of at least one pentose, hexose or a combination thereof (excluding xylose, rhamnose or a combination thereof). Examples of the pentose and hexose are as described above. The UDP-sugar is preferably UDP-hexose, and more preferably, a hexose selected from the group consisting of glucose, mannose and galactose. The UDP-sugar described above is most preferably UDP-glucose.

The method for producing the steviol glycoside in accordance with the present invention comprises the step of reacting the protein of the invention, the UDP-sugar and the compound represented by general formula (I) to add the sugar molecule to the carboxyl at position 19 of the compound represented by general formula (I). Method 1 of the present invention may further include the step of purifying the steviol glycoside produced in the step above.

Examples of the steviol glycoside produced by the production method of the present invention include, but not limited to, steviolbioside, stevioside, rebaudioside A, rebaudioside B, rebaudioside C, rebaudioside D, rebaudioside E, rebaudioside F, or a combination thereof.

The steviol glycoside produced may be purified by known techniques including extraction with an appropriate solvent (an aqueous solvent such as water, etc., or an organic solvent such as alcohol, ether, acetone, etc.), a gradient with ethyl acetate or other organic solvent: water, high performance liquid chromatography (HPLC), gas chromatography, time-of-flight mass spectrometry (TOF-MS), ultra high performance liquid chromatography (UPLC), etc.

2. Non-Human Transformant with High Steviol Glycoside Level

The steviol glycoside may also be produced in cells from bacteria (*Escherichia coli*, yeast, etc.), plants, insects, mammals except human, etc., using the protein of the present invention. This is because the protein of the present invention is an enzyme derived from *stevia* or a variant thereof and thus expected to retain its high activity even under intracellular environment. In this case, the steviol glycoside can be produced by introducing a polynucleotide encoding the protein of the present invention (cf., "the polynucleotide of the present invention" as described later) into host cells derived from bacteria, plants, insects, mammals except human, etc. to express the protein of the present invention and reacting the protein of the present invention, the UDP-sugar present in the cells above and the compound represented by general formula (I).

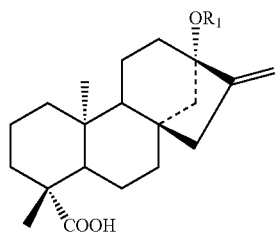

(I)

Thus, the present invention provides a non-human transformant, into which a polynucleotide selected from the group consisting of (a) to (e) below is introduced (hereinafter referred to as "the transformant of the present invention"):

(a) a polynucleotide comprising the nucleotide sequence of SEQ ID NO: 1;

(b) a polynucleotide encoding a protein consisting of the amino acid sequence of SEQ ID NO: 2;

(c) a polynucleotide encoding a protein consisting of an amino acid sequence wherein 1 to 48 amino acids are deleted, substituted, inserted and/or added in the amino acid sequence of SEQ ID NO: 2, and having an activity of adding a sugar molecule to the carboxyl at position 19 of a compound represented by general formula (I) below;

(d) a polynucleotide encoding a protein having an amino acid sequence having at least 90% sequence identity with the amino acid sequence of SEQ ID NO: 2, and having an activity of adding a sugar molecule to the carboxyl at position 19 of a compound represented by general formula (I) below; and, (e) a polynucleotide that hybridizes under highly stringent conditions with a polynucleotide consisting of a nucleotide sequence complementary to the nucleotide sequence of SEQ ID NO: 1 and encodes a protein having an activity of adding a sugar molecule to the carboxyl at position 19 of the compound represented by general formula (I).

The definition and specific examples of general formula (I) are the same as already described above, and the definition and specific examples of the sugar molecule added to the carboxyl at position 19 of the compound represented by general formula (I) are also the same as described above.

As used herein, the term "polynucleotide" is intended to mean a DNA or RNA.

As used herein, the term "polynucleotide which hybridizes under highly stringent" refers to, e.g., a polynucleotide consisting of a nucleotide sequence complementary to the nucleotide sequence of SEQ ID NO: 1, or a polynucleotide obtained by the colony hybridization method, plaque hybridization method, Southern hybridization method or the like, using as a probe the whole or part of a polynucleotide consisting of the nucleotide sequence encoding the amino acid sequence of SEQ ID NO: 2. For the methods of hybridization, there are used the methods described in, e.g., "Sambrook & Russell, Molecular Cloning; A Laboratory Manual Vol. 3, Cold Spring Harbor, Laboratory Press 2001" and "Ausubel, Current Protocols in Molecular Biology, John Wiley & Sons 1987-1997," etc.

As used herein, the term "highly stringent conditions" are conditions, for example, (1) 5×SSC, 5×Denhardt's solution, 0.5% SDS and 50% formamide at 50° C., (2) 0.2×SSC and 0.1% SDS at 60° C., (3) 0.2×SSC and 0.1% SDS at 62° C., (4) 0.2×SSC and 0.1% SDS at 65° C., or (5) 0.1×SSC and 0.1% SDS at 65° C., but not limited thereto. Under these conditions, a DNA with higher sequence identity may be expected to be obtained efficiently at higher temperatures, although multiple factors are involved in hybridization stringency including temperature, probe concentration, probe length, ionic strength, time, salt concentration and others, and those skilled in the art may appropriately select these factors to achieve similar stringency.

When commercially available kits are used for hybridization, for example, an Alkphos Direct Labeling and Detection System (GE Healthcare) may be used. In this case, according to the attached protocol, after incubation with a labeled probe overnight, the membrane is washed with a primary wash buffer containing 0.1% (w/v) SDS at 55 to 60° C., thereby detecting hybridized DNA. Alternatively, in producing a probe based on the nucleotide sequence complementary to the nucleotide sequence of SEQ ID NO: 1 or on the entire or part of the nucleotide sequence encoding the amino acid sequence of SEQ ID NO: 2, hybridization can be detected with a DIG Nucleic Acid Detection Kit (Roche Diagnostics) when the probe is labeled with digoxigenin (DIG) using a commercially available reagent (e.g., a PCR Labeling Mix (Roche Diagnostics), etc.).

In addition to those described above, other polynucleotides that can be hybridized include DNAs having 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher or 99.9% or higher identity with the DNA of SEQ ID NO: 1, or the DNA encoding the amino acid sequence of SEQ ID NO: 2, as calculated by homology search software, such as FASTA and BLAST using default parameters.

Identity between amino acid sequences or nucleotide sequences may be determined using FASTA (Science 227 (4693): 1435-1441, (1985)), algorithm BLAST (Basic Local Alignment Search Tool) by Karlin and Altschul (Proc. Natl. Acad. Sci. USA, 87: 2264-2268, 1990; Proc. Nail Acad. Sci. USA, 90: 5873, 1993). Programs called blastn, blastx, blastp, tblastn and tblastx based on the BLAST algorithm have been developed (Altschul S. F. et al, J. Mol. Biol. 215: 403, 1990). When a nucleotide sequence is sequenced using blastn, the parameters are, for example, score=100 and wordlength=12. When an amino acid sequence is sequenced using blastp, the parameters are, for example, score=50 and wordlength=3. When BLAST and Gapped BLAST programs are used, default parameters for each of the programs are employed.

The polynucleotides of the present invention described above can be acquired by known genetic engineering techniques, known methods for synthesis, and so on.

The polynucleotides of the present invention is introduced into a host, preferably, in such a state that it is inserted into an appropriate expression vector.

The appropriate vector is generally constructed to contain an expression cassette comprising:

(i) a promoter that can be transcribed in a host cell;

(ii) any of the polynucleotides of the present invention that is linked to the promoter; and, (iii) an expression cassette comprising as a component a signal that functions in the host cell with respect to the transcription termination and polyadenylation of RNA molecule.

To construct the expression vector, procedures using a plasmid, phage or cosmid are used but are not particularly limited thereto.

Vectors are not particularly limited to any specific type, and those capable of expressing in a host cell can be suitably chosen. That is, a suitable promoter sequence may be chosen depending upon the type of a host cell to reliably express the polynucleotide of the invention, and a vector obtained by incorporating this sequence and the polynucleotide of the present invention into various plasmids or the like may be used as an expression vector.

The expression vector of the present invention contains an expression control region (e.g., a promoter, a terminator, and/or a replication origin, etc.) depending on the type of a host to be introduced. A conventional promoter (e.g., trc promoter, tac promoter, lac promoter, etc.) is used as the promoter for a bacterial expression vector. As the promoter for yeast, there are used, for example, GAL1 promoter, GAL10 promoter, glyceraldehyde 3-phosphate dehydrogenase promoter, PH05 promoter, etc. As the promoter for fungi there are used, for example, amylase, trpC, etc. Furthermore, examples of the promoter for expressing the gene of interest in plant cells include cauliflower mosaic virus 35S RNA promoter, rd29A gene promoter, rbcS promoter, mac-1 promoter wherein an enhancer sequence of the cauliflower mosaic virus 35S RNA promoter above is added to the 5' end of mannopine synthetase promoter sequence from *Agrobacterium*, etc. Viral promoter (e.g., SV40 early promoter, SV40 late promoter, etc.) are used as the promoter for animal-derived host cells.

Preferably, the expression vector contains at least one selection marker. As such a selection marker, there may be used auxotrophic markers (ura5, niaD, TRP1, URA3, HIS3, LEU2), chemical-resistant markers (hygromycin, zeocin), genecitin-resistant gene (G418r), copper-resistant gene (CUP 1) (Marin et al., Proc. Natl. Acad. Sci. USA, 81, p. 337 1984), cerulenin-resistant gene (fas2m, PDR4) (Junji Inokoshi, et al., Biochemistry, 64, p. 660, 1992; and Hussain et al., Gene, 101: p. 149, 1991, respectively), etc.

A method of preparing (method of producing) the transformant of the present invention is not particularly limited and includes, e.g., a method which comprises introducing the expression vector bearing the polynucleotide of the present invention into a host for transformation.

The transformant of the present invention is expected to produce the steviol glycoside with a high efficiency. Host cells used for transformation are not particularly limited and various cells can be advantageously used. Examples of the host cells are bacteria such as *Escherichia coli*, etc., yeast (*Saccharomyces cerevisiae, Schizosaccharomyces pombe*, plant cells, animal cells except human, etc.

Host cells are preferably host cells capable of producing the compound represented by general formula (I) (preferably, steviolmonoside, steviolbioside or steviol). Herein, the host cells are not limited to those capable of producing the compound represented by general formula (I) in a natural state, and may also include those genetically engineered by known genes so that the compound represented by general formula (I) can be produced.

The genes encoding the enzymes that contribute to synthesis of the compound represented by general formula (I) include known genes such as EK13H, UGT74G1 and UGT76G1 (Non-Patent Document 2), but are not limited thereto.

Where host cells are those incapable of producing the compound represented by general formula (I), the gene of the present invention is introduced into the host cells and the compound represented by general formula (I) (preferably, steviolmonoside, steviolbioside or steviol) or a plant extract containing the compound is added as a substrate to the culture system of the resulting transformant. Steviol glycosides can thus be produced even without introducing the gene encoding the enzyme which contributes the compound represented by general formula (I).

Culture media and conditions suitable for the host cells above are well known in the art. The organism to be transformed is not particularly limited, and includes various microorganisms, plants and animals other than human, which given as examples of the host cells above.

For transformation of host cells, there may be used generally known methods. The transformation can be performed by the electroporation method (Mackenzie D. A. et al., Appl. Environ. Microbiol., 66, 4655-4661, 2000), the particle delivery method (JPA 2005-287403), the spheroplast method (Proc. Natl. Acad. Sci. USA, 75 p. 1929 (1978)), the lithium acetate method (the methods described in J. Bacteriology, 153 p. 163 (1983)), Methods in yeast genetics, 2000 Edition: A Cold Spring Harbor Laboratory Course Manual, etc.), but is not limited thereto.

In addition, reference may be made to "Sambrook & Russell, Molecular Cloning: A Laboratory Manual Vol. 3, Cold Spring Harbor Laboratory Press 2001," "Methods in Yeast Genetics, A laboratory manual (Cold Spring Harbor Laboratory Press, Cold Spring Harbor, N.Y.)," etc., for general molecular biological techniques.

The steviol glycoside can be produced by the transformant through incubation of the transformant thus obtained. As described above, the compound of general formula (I) or a plant extract containing the compound may also be added the culture system of the transformant as a substrate to promote production of the steviol glycoside. The steviol glycoside accumulated may be extracted and purified to give the steviol glycoside of interest.

Thus, the present invention provides Method 2 for producing the steviol glycoside, which comprises using the transformant of the present invention. Suitable culture media and conditions are well known in the art. The procedures for extraction and purification of the steviol glycoside are already described.

The steviol glycoside is not particularly limited, and preferably may be one selected from the group consisting of steviolbioside, stevioside, rebaudioside A, rebaudioside B, rebaudioside C, rebaudioside D, rebaudioside E, rebaudioside F, or a combination thereof.

In a further embodiment of the present invention, the transformant may be a transformant plant. The transformant plant according to this embodiment may be obtained by introducing a recombinant vector comprising the polynucleotide of the present invention into a plant to express a polypeptide encoded by the polynucleotide.

Where a recombinant expression vector is used, the recombinant expression vector used to transform the plant is not particularly limited as far as the vector is capable of expressing the polynucleotide of the present invention in said plant. Examples of such vectors include a vector bearing a promoter capable of constitutively expressing the polynucleotide in plant cells, and a vector bearing a promoter inducibly activated by external stimulation.

Examples of the promoter constitutively expressing the polynucleotide in plant cells include 35S RNA promoter of cauliflower mosaic virus, rd29A gene promoter, rbcS promoter, mac-1 promoter, etc.

Examples of the promoter inducibly activated by external stimulation include mouse mammary tumor virus (MMTV) promoter, tetracycline-responsive promoter, metallothioinene promoter, heat shock protein promoter, etc.

Plants that are subject to transformation in the present invention are intended to mean entire plant bodies, plant organs (e.g., leaves, petals, stems, roots, seeds, etc.), plant tissues (e.g., epidermis, phloem, parenchyma, xylem, vascular bundles, palisade tissues, spongy tissues, etc.) or plant culture cells, or may be any of various types of plant cells (e.g., suspension culture cells), protoplasts, leaf slices, calli, and the like. Plant species which are used for transformation are not particularly limited and may be any plant from those belonging to the Monocotyledoneae or the Dicotyledoneae.

Conventional transformation methods (e.g., the *Agrobacterium* method, gene gun method, PEG method, electroporation method, etc.) known to those ordinarily skilled in the art are used for gene transfer to plants. For example, the *Agrobacterium*-mediated method and the method of directly introducing into plant cells are well known. When the *Agrobacterium* method is used, the plant expression vector constructed is introduced into an appropriate *Agrobacterium* strain (e.g., *Agrobacterium tumefaciens*) and this strain is infected to aseptically cultured leaf discs according to the leaf disc method (Hirobumi Uchimiya, Manuals for Plant Gene Manipulation (1990), pp. 27-31, Kodansha Scientific Co., Ltd., Tokyo), etc. to give transgenic plants. The method by Nagel, et al. (Micribiol. Lett., 67: 325 (1990)) may also be used. This method involves introducing first, e.g., an expression vector into *Agrobacterium* and then introducing the transformed *Agrobacterium* into plant cells or plant tissues by the method described in Plant Molecular Biology Manual (Gelvin, S. B. et al., Academic Press Publishers). Herein, the "plant tissue" includes calli obtained by culturing plant cells. When the transformation is carried out using the *Agrobacterium* method, binary vectors (pBI121 or pPZP202, etc.) may be used.

For direct transfer of genes to plant cells or plant tissues, the electroporation method and the particle gun method are known. When a particle gun is used, plant bodies, plant organs or plant tissues per se may be used, or slices may be prepared and then provided for use, or protoplasts may also be prepared and then provided for use. The samples thus prepared can be bombarded using a gene transfer apparatus (e.g., PDS-1000 (BIO-RAD, Inc.), etc.). Bombardment conditions may vary depending upon plants or samples. Normally, the bombardment is performed under a pressure of about 450 to 2000 psi at a distance of about 4 to 12 cm.

The cells or plant tissues into which the gene is introduced are first selected for their chemical resistance such as hygromycin resistance, etc. and then regenerated into plant bodies in a conventional manner. Regeneration of plant bodies from the transformants can be performed by methods known to those skilled in the art, depending upon species of plant cells.

Where a plant culture cell is used as a host, transformation is performed by introducing the recombinant vector into culture cells by the gene gun method, the electroporation method, etc. Calluses, shoots, hairy roots, etc. resulted from the transformation can be used directly in cell culture, tissue culture or organ culture. Furthermore, they can be regenerated into plant bodies by conventional plant tissue culture methods through administration of plant hormones (e.g., auxin, cytokinin, gibberellin, abscisic acid, ethylene, brassinolide, etc.) at appropriate concentrations.

Whether or not the polynucleotide of the present invention has been introduced into the plant can be confirmed by PCR, Southern hybridization, northern hybridization or the like. For example, DNA is prepared from the transgenic plant and then DNA-specific primers are designed to perform PCR. PCR can be performed under the same conditions as used for the preparation of plasmids described above. Subsequently, the amplified product is subjected to agarose gel electrophoresis, polyacrylamide gel electrophoresis, capillary electrophoresis, etc. and stained with ethidium bromide, SYBR Green solution, etc. By detecting the amplified product as a single band, it can be confirmed that the host has been transformed. Alternatively, PCR may be performed using primers previously labeled with a fluorescent dye or the like, and the amplified product can be detected. Furthermore, there may be employed a method which involves binding the amplified product to a solid phase such as a microplate, etc. and then confirming the product by fluorescence or enzyme reactions.

Once the transgenic plant wherein the polynucleotide of the present invention has been incorporated into the genome is acquired, its progeny can be obtained by sexual or asexual reproduction of the plant body. Furthermore, the plant body can be mass-produced by acquiring from the plant body or its progeny or clones thereof, e.g., seeds, fruits, cut panicles, tubers, tuberous roots, strains, calli, protoplasts, etc., and then using them as the origin. Accordingly, the present invention also encompasses the plant body in which the polynucleotide in accordance with the present invention is expressibly introduced, or progenies of the plant body having the same property as in the plant body, and tissues derived therefrom.

The transformation methods for various plants are already reported. Examples of the transgenic plants in accordance with the present invention include, but not be limited to, solanaceous plants (e.g., eggplant, tomato, green pepper, potato, tobacco, datura or downy thorn apple, alkakengi, petunia, *Calibrachoa* sp., *nierembergia*, etc.), leguminous plants (e.g., soybean, azuki bean, peanut, common bean or *Phaseolus vulgaris*, broad bean, *Lotus japonicus*, etc.), rosaceous plants (e.g., strawberry, plum, cherry, rose, blueberry, blackberry, bilberry, cassis, raspberry, *Rubus suauissimus*, etc.), caryophyllaceous plants (carnation, soap root, etc.), *chrysanthemum* plants (*chrysanthemum, gerbera*, sunflower, daisy, *stevia*, etc.), orchidaceous plants (orchid, etc.), primulaceous plants (cyclamen, etc.), gentianaceous plants (lisianthus, gentian, etc.), iridaceous plants (freesia, iris, *gladiolus*, etc.), scrophulariaceous plants (*antirrhinum*, torenia, etc.), *Kalanchoe pinnata* (*Kalanchoe*), liliaceous plants (lily, tulip, etc.), convolvulaceous plants (morning glory, cairo morning glory, moonflower, sweet potato, *Ipomoea quamoclit*, Evolvulus or American blue, etc.), *hydrangea* plants (*hydrangea*, deutzia, etc.), cucurbitaceous plants (bottle gourd, etc.), geraniaceous plants (*pelargonium*, geranium, etc.), oleaceous plants (forsythia, etc.), vitaceous plants (e.g., grapevine, etc.), theaceous plants (*camellia*, tea, etc.), poaceous plants (e.g., rice plant, barley, wheat, oat, rye, sweet corn, foxtail millet, Japanese millet, kaoliang, sugar cane, bamboo, oat, finger millet, sorghum, Indian rice, Job's tears, pasture grass, etc.), moraceous plants (mulberry, hopvine, kouzo or paper mulberry, rubber tree, *Cannabis*, etc.), rubiaceous plants (Arabian coffee, *gardenia*, etc.), fagaceous plants (oak, Buna or Japanese beech, Kashiwa oak, etc.), Pedaliaceae plants (sesame, etc.), rutaceous plants (e.g., daidai orange, yuzu lemon, unshu citrus, Japanese prickly ash), brassicaceous plants (red cabbage, flowering cabbage, Japanese radish, *Arabidopsis*, rapeseed, cabbage, broccoli, cauliflower, etc.), and Lamiaceae plants (*salvia*, Japanese basil, lavender, skull cap, etc.). Particularly preferred examples of the plant for transformation include plants that are known to biosynthesize various glycosides using steviol as the aglycon. Such plants include *stevia*, *Rubus suauissimus*, and the like.

The plant transformed by the polynucleotide of the present invention (hereinafter "the plant of the present invention" or "the plant body of the present invention") can produce steviol glycosides in a higher quantity, as compared with its wild type, so long as it has an appropriate substrate or when an appropriate substrate is externally added.

The plant of the present invention can easily provide a complete plant by cultivating the seeds, cuttings, bulbs, etc. from the plant of the present invention.

Consequently, the plant of the present invention includes entire plant bodies, plant organs (e.g., leaves, petals, stems, roots, seeds, bulbs, etc.), plant tissues (e.g., epidermis, phloem, parenchyma, xylem, vascular bundles, palisade tissues, spongy tissues, etc.) or plant culture cells, or various types of plant cells (e.g., suspension culture cells), protoplasts, leaf slices, calli, and the like.

3. Extract of the Transformant and Use Thereof

In a still further embodiment, the present invention provides an extract of the transformant described above. When it has an appropriate substrate or when an appropriate substrate is externally added, the transformant of the present invention is expected to have a high content of steviol glycosides in its extract, as compared with its wild type.

The transformant of the present invention can be obtained by disrupting the transformant using glass beads, a homogenizer, a sonicator, etc., centrifuging the disrupted product and then recovering the supernatant. An additional step of extraction may also be performed by the procedures for extracting steviol glycosides described above.

The extract of the transformant of the present invention can be used to produce, e.g., food products, pharmaceuticals, industrial materials, and the like.

In a yet further embodiment, the present invention provides foods, pharmaceuticals and industrial materials (raw materials for food, etc.) containing the extract of the transformant of the present invention. The foods, pharmaceuticals and industrial materials containing the extract of the transformant of the present invention may be prepared in a conventional manner. As such, the food products, pharmaceuticals, industrial materials, etc., containing the extract of the transformant of the present invention contains the steviol glycoside produced using the transformant of the present invention.

The food of the present invention includes, for example, a dietary supplement, health food, functional food, food product for young children, geriatric food, etc. As used herein, the food or food product is intended to mean a solid, fluid and liquid food as well as a mixture thereof, and collectively means an edible stuff.

The term dietary supplement refers to food products enriched with specific nutritional ingredients. The term health food refers to food products that are healthful or good for health, and encompasses dietary supplements, natural foods, diet foods, etc. The term functional food refers to a food product for replenishing nutritional ingredients which assist body control functions. Functional foods are synonymous with foods for specified health use. The term food for young children refers to a food product given to children up to about 6 years old. The term geriatric food refers to a food product treated to facilitate digestion and absorption when compared to untreated foods.

In the food product of the present invention, the non-caloric steviol glycoside is used as a sweetener. Accordingly, the food product of the present invention is low calorie and have the advantage that contributes to health promotion or health maintenance.

The shape of these food products may include, for example, bread, noodles, pasta, rice, confectionery (cake, ice cream, ice candy, doughnut, baked cookie, candy, chewing gum, gummy candy and tablet, as well as Japanese confectionery such as rice dumpling, bean paste cake, etc.), agricultural foods such as tofu (soybean curd) and its processed products, etc., fermented foods such as Japanese sake (rice wine), medicinal liquor, mirin (sweet cooking sherry), vinegar, soy sauce, miso (bean paste), etc., livestock food products such as yoghurt, ham, bacon, sausage, etc.; seafood products such as kamaboko (minced and steamed fish), ageten (deep-fried fish cake), hanpen (puffy fish cake), etc., as well as fruit drinks, soft drinks, sports drinks, alcoholic beverages, tea, condiments. The shape of the food products may also include, for example, low-calorie beverage, non-sugar beverage, fruit can, milk beverage, powder beverage, yoghurt, jelly, dressing, men-tsuyu (soy sauce-based seasoning liquid for noodle), Japanese pickle, tsukudani (sea foods boiled in soy sauce), soy sauce, miso (bean paste), shiokara (salted fish guts), Vermont vinegar, pickled shallots in sugared vinegar, sweet pickled ginger, *lotus* roots pickled in vinegar, Japanese pickles, soy-based sweet sauce for tempura and broiled kabayaki eel, grilled meat sauce, sauce, etc., gum, candy and lollipop, toothpaste, satsuma-age (fried fish cake), dashi-maki (rolled omelet), sauce for pan-fried noodle, sauce for cold noodles, shimesaba (vinegared mackerel fillet), ices, sherbet, soft cream, fish jelly products, refreshments, rice cake, cone cup, seasoned laver, tenkasu (crunchy bits of tempura), furikake (rice seasoning), etc.

Dosage form of the pharmaceutical (composition) of the present invention is not particularly limited and may be any dosage form including the state of a solution, paste, gel, solid or powder. Also, the pharmaceutical composition of the present invention may be used as topical agents for the skin, including an oil, lotion, cream, emulsion, gel, shampoo, hair rinse, hair conditioner, enamel, foundation, lipstick, face powder, facial pack, ointment, powder, tooth paste, aerosol, cleansing foam, etc., bath agent, medicated tonic, skin beauty essence, sun protectant, etc.

The pharmaceutical composition of the present invention may further contain other pharmaceutically active components (e.g., antiinflammatory components) or aid components (e.g., lubricant or carrier components).

4. Method for Screening a Plant with a High Content of Steviol Glycosides

The present invention provides a method for screening a plant with a high content of steviol glycosides. Specifically, the method above comprises steps (1) to (3) below:

(1) a step of extracting mRNA from a test plant;
(2) a step of hybridizing said mRNA or cDNA prepared from said mRNA to a polynucleotide that hybridizes under highly stringent conditions with a polynucleotide consisting of a nucleotide sequence complementary to the polynucleotide of the present invention; and,
(3) a step of detecting said hybridization.

The step (1) described above may be performed by extracting mRNA from a test plant. The site of the test plant, from which mRNA is to be extracted, is not particularly limited and preferably, petals. When mRNA is extracted, cDNA may be prepared from mRNA by reverse transcription.

The step (2) can be performed by hybridizing the extracted mRNA above under highly stringent conditions using as a probe or primer a polynucleotide or oligonucleotide consisting of a nucleotide sequence complementary to the polynucleotide of the present invention. The highly stringent conditions are as described above. The polynucleotide or oligonucleotide has a length of preferably 5 to 500 bp, more preferably, 10 to 200 bp, and most preferably, 10 to 100 bp. The polynucleotide or oligonucleotide may be easily synthesized using various automated synthesizer (e.g., AKTA oligopilot plus 10/100 (GE Healthcare)). Alternatively, the synthesis may also be entrusted to a third-party organization (e.g., Promega Inc., or Takara Co.), etc.

Where the polynucleotide consisting of the nucleotide sequence complementary to the polynucleotide of the present invention is used as a probe in the step (2), the step (3) can be performed by ordinary methods for detecting hybridization, including Southern blotting, northern blotting (Sambrook, Fritsch and Maniatis, "Molecular Cloning: A Laboratory Manual" 2nd Edition (1989), Cold Spring Harbor Laboratory Press), Microarray (Affymetrix Inc.; cf., U.S. Pat. Nos. 6,045,996, 5,925,525 and 5,858,659), TaqMan PCR (Sambrook, Fritsch and Maniatis, "Molecular Cloning: A Laboratory Manual" 2nd Edition (1989), Cold Spring Harbor Laboratory Press), Fluorescent In Situ Hybridization (FISH) (Sieben V. J. et al., (2007-06). IET Nanobiotechnology 1 (3): 27-35), etc. On the other hand, where the polynucleotide consisting of the nucleotide sequence complementary to the polynucleotide of the present invention is used as a primer in the step (2), the hybridization can be detected in the step 3 by performing PCR amplification and analyzing the resulting amplification product through electrophoresis or sequencing (Sambrook, Fritsch and Maniatis, "Molecular Cloning: A Laboratory Manual" 2nd Edition (1989), Cold Spring Harbor Laboratory Press), etc.

The plant body that hybridization is detected at a higher level is considered to express the protein having the activity of adding the sugar molecule to the carboxyl at C19-position of the compound represented by general formula (I) below more abundantly than in other plant bodies, and thus expected to have a higher content of the steviol glycoside.

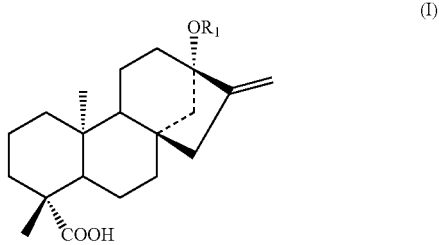

(I)

EXAMPLES

Hereinafter, the present invention will be described more specifically with reference to EXAMPLES below but is not deemed to be limited thereto.

[Example 1] Isolation of Candidate Gene for Steviolbioside Glucosyltransferase

In the prior publication (Non-Patent Document 2), it is reported that UGT85C2 (GENBANK Accession No. AY345978) has the activity of transferring one molecule of glucose to the C-13 hydroxyl of steviol to form steviolmonoglucoside. In order to obtain the UGT85C2 gene, PCR was performed with the following primer set (SEQ ID NOS: 3 and 4) using as a template cDNA prepared from stevia leaves.

Stevia leaf cDNA was obtained by extracting total RNA from stevia leaves using an RNeasy Plant Mini Kit (QIAGEN) and subjecting 0.5 µg of the total RNA to reverse transcription (RT) with Random Oligo-dT primer CACC-NdeI-SrUGT85C2-Fw (the underlined portion is the NdeI recognition site):

(SEQ ID NO: 3)
5'-CACC<u>CATATG</u>GATGCAATGGCTACAACTGAGAA-3'

BglII-SrUGT85C2-Rv (the underlined portion is the BglII recognition site):

(SEQ ID NO: 4)
5'-<u>AGATCT</u>CTAGTTTCTTGCTAGCACGGTGATTT-3'

A PCR solution (50 µl) had the composition of 1 µl of cDNA from stevia leaves, 1× ExTaq buffer (TaKaRaBio), 0.2 mM dNTPs, 0.4 pmol each/µl of the primers and 2.5U ExTaq polymerase. PCR was performed by reacting at 94° C. for 3 minutes, and then amplifying for a total of 30 cycles of the reaction at 94° C. for 1 minute, 50° C. for 1 minute and 72° C. for 2 minutes. The PCR product was electrophoresed on a 0.8% agarose gel, followed by staining with ethidium bromide. As a result, the amplified band was detected at a size of about 1.4 kb, predicted from each template DNA.

This PCR product was subcloned into a pENTR-TOPO Directional Vector (Invitrogen) by the procedure recommended by the manufacturer. Using a DNA Sequencer Model 3100 (Applied Biosystems), primer walking was performed with a synthetic oligonucleotide primer to determine the sequence.

As a result, the obtained DNA sequence showed the sequence identity with the reported UGT85C2 (Non-Patent Document 2) at 99% of the DNA level (different in 3 nucleotides) and at 99% of the putative amino acid level (different in 3 amino acids) (CDS sequence: SEQ ID NO: 1, amino acid sequence: SEQ ID NO: 2).

[Example 2] Construction of Expression Vector

The ORF fragment of about 1.4 kb from UGT85C2 was excised using the restriction enzyme sites of NdeI and BglII (the underlined portions of SEQ ID NOS: 3 and 4) added to the primer, and ligated into the NdeI and BglII sites of Escherichia coli expression vector pET15b (Novagen, Inc.) to give Escherichia coli expression vector of this enzyme gene. His tag located upstream the NdeI site of the vector matched with the open reading frame of UGT85C2 gene; it was designed to express the chimeric protein of UGT85C2 fused to His tag.

[Example 3] Expression and Purification of the Recombinant Protein

To clarify the biochemical functions of the enzyme, the enzyme was expressed in Escherichia coli. Using the UGT85C2 Escherichia coli expression plasmid obtained above, Escherichia coli BL21 (DE3) was transformed. The resulting transformants were shake-cultured in 4 ml of LB medium (10 g/l tryptone peptone, 5 g/l yeast extract and 1 g/l NaCl) containing 50 µg/ml of ampicillin at 37° C. overnight. When reached the stationary phase, 4 ml of the culture broth was inoculated onto 80 ml of a medium with the same composition, followed by shake culture at 37° C. IPTG was added in a final concentration of 0.5 mM at the point when the cell turbidity (OD600) reached approximately 0.5. Shake culture was continued at 18° C. for 20 hours.

The following procedures were all performed at 4° C. The transformants cultured were collected by centrifugation (5,000×g, 10 mins.), and suspended by adding 1 ml/g cell of Buffer S [20 mM HEPES buffer (pH 7.5), 20 mM imidazole and 14 mM β-mercaptoethanol]. The suspension was then ultrasonicated (15 secs.×8 times), followed by centrifugation (15,000×g, 15 mins.). The resulting supernatant was recovered as a crude enzyme solution. The crude enzyme solution was loaded onto a His SpinTrap (GE Healthcare), which had been equilibrated with Buffer S, and then centrifuged (70× g, 30 secs.). After washing with the buffer, the protein bound to the column was eluted stepwise with 5 ml each of Buffer S containing 100 mM and 500 mM imidazole. In each of the eluted fractions, the buffer was replaced through a Microcon YM-30 (Amicon) by 20 mM HEPES buffer (pH 7.5) and 14 mM β-mercaptoethanol (magnification of dialysis, ×1000).

As a result of the SDS-PAGE separation followed by CBB staining, the protein was confirmed in the fraction eluted with 500 mM imidazole at approximately 50 KDa of the estimated molecular weight for the HisTag-fused UGT85C2 chimeric protein. This fraction was used for the enzyme analysis (FIG. 2).

[Example 4] Assay for Enzyme Activity of UGT85C2

Standard conditions for the enzyme reaction were as follows. A reaction solution (2 mM UDP-glucose, 0.1 mM glycosyl acceptor substrate (steviol), 100 mM potassium phosphate buffer (pH 7.0) and 25 µl of purified UGT85C2 enzyme solution) was prepared in distilled water to become 50 µl, and reacted at 30° C. for an hour. The LC-MS analysis was performed for 5 µl of the enzyme reaction solution under the following conditions.

LC Conditions

Column: Waters Sunfire C18 3.5 um 2.0 mm I.D.×20 mm

Moving phase: A: MilliQ Water (+0.05% formic acid), B: MeCN

Gradient: linear gradient of B from 15% to 55% (20 mins.)

Flow rate: 0.2 ml/min.

Column oven: 40° C.

MS Conditions

ESI (negative mode)

Selected ion monitoring: m/z 317, 479, 641, 687, 803 and 849

Figure 4:
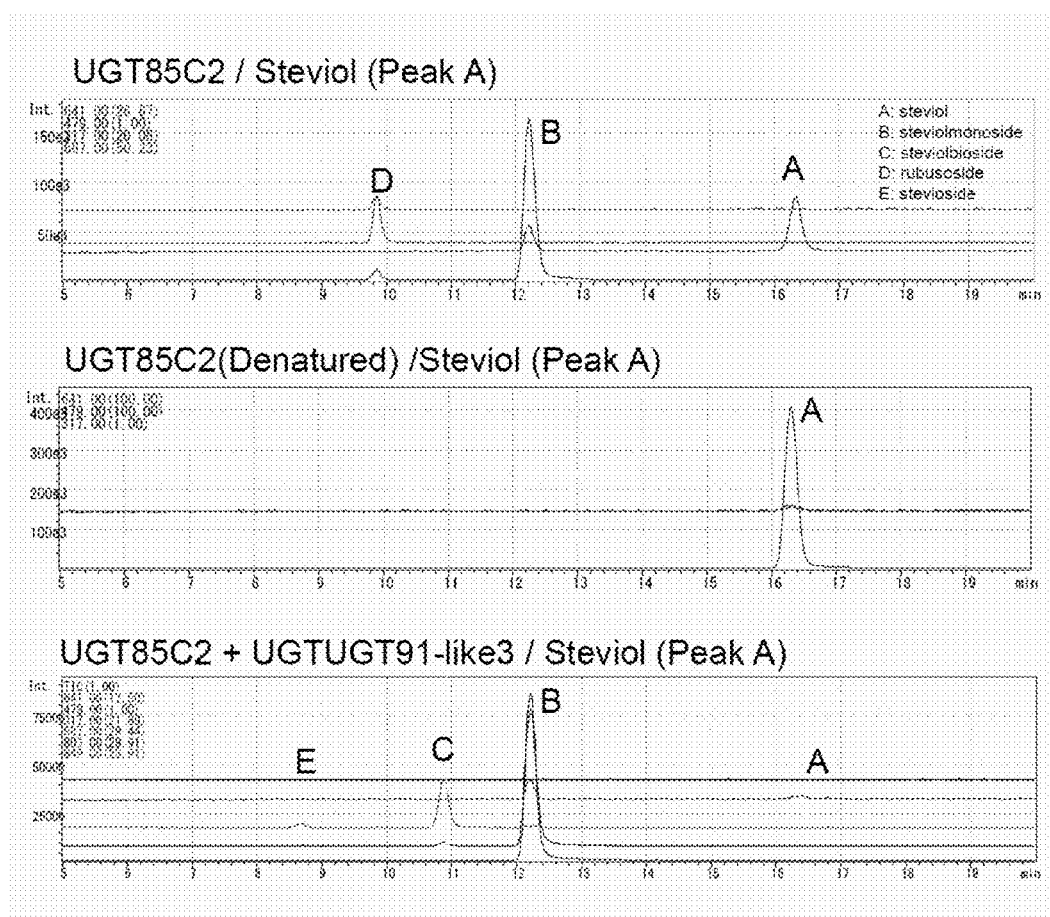
FIG. 4 shows the glycosyltransferase activity of UGT85C2 protein on steviol.
Figure 5:
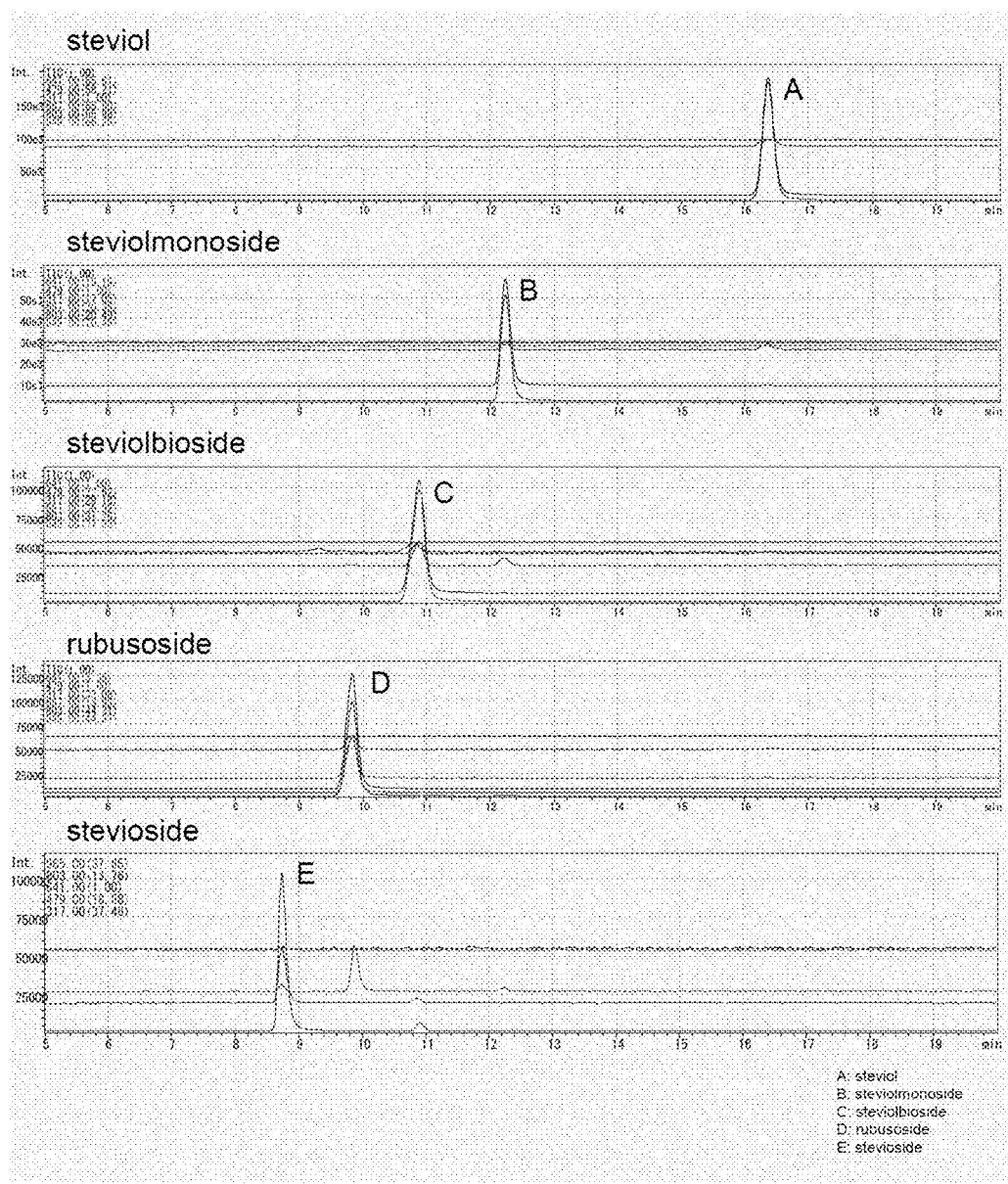
FIG. 5 shows the chromatogram of standard steviol glycoside.

UGT85C2 was reacted with steviol. As a result, it was confirmed that the hydroxyl group at C-13 position of steviol was glucosylated (FIG. 4, panel 1: peak A) to form steviolmonoside (FIG. 4, panel 1: peak B). It was also confirmed that rubusoside (FIG. 4: panel 1: peak D) with the carboxyl at C19-position being glucosylated was additionally formed simultaneously in the reaction solution (FIG. 4: panel 1). The two products were not detected in the reaction solution with the UGT85C2 protein that had been inactivated by thermal denaturation (FIG. 4: panel 2). Thus, the products were both confirmed to be the reaction products with the UGT85C2 enzyme. It was also confirmed that steviolbioside (FIG. 4: panel 3: peak C) and stevioside (FIG. 4: panel 3: peak E) were formed by the simultaneous reaction of UGT85C2 and UGT91D-like 3 (CDS sequence: SEQ ID NO: 5, amino acid sequence: SEQ ID NO: 6) (FIG. 4: panel 3). Thus, there was a new finding that the UGT85C2 protein glucosylates the hydroxyl at C13-position of steviol and at the same time, also glucosylates the carboxyl at C19-position of steviolbioside. These results of the enzyme analysis suggest that in stevia, stevioside (FIG. 4: panel 3: peak E) has two pathways for biosynthesis via steviolbioside (FIG. 4: panel 3: peak C) and rubusoside (FIG. 4: panel 1: peak D).

INDUSTRIAL APPLICABILITY

According to the present invention, the carboxyl at C19-position of steviolmonoside and steviolbioside can be glycosylated using the UGT85C2 gene and the sweetness and quality of taste of steviol glycosides can be improved. The present invention has clarified the whole picture of the biosynthetic pathway up to rebaudioside A, and provides a molecular tool for producing non-caloric natural sweeteners rebaudioside A, stevioside and other analogous compounds not only in plants but also in microorganisms.

SEQUENCE LISTING FREE TEXT

SEQ ID NO: 3: synthetic DNA

SEQ ID NO: 4: synthetic DNA

The invention claimed is:

1. A polynucleotide selected from:
   a polynucleotide comprising the nucleotide sequence of SEQ ID NO: 1; and
   a polynucleotide comprising a heterologous regulatory element operably linked to a polynucleotide sequence encoding a protein consisting of the amino acid sequence of SEQ ID NO: 2.

2. A non-human transformant comprising the polynucleotide of claim 1.

3. The non-human transformant according to claim 2, which is a plant.

4. A method comprising culturing or cultivating the non-human transformant according to claim 2 to produce the protein consisting of the amino acid sequence of SEQ ID NO: 2.

5. The method of claim 4, further comprising:
   producing a steviol glycoside by contacting the protein consisting of the amino acid sequence of SEQ ID NO: 2 produced by the non-human transformant with a UDP-sugar and a compound represented by formula (I):

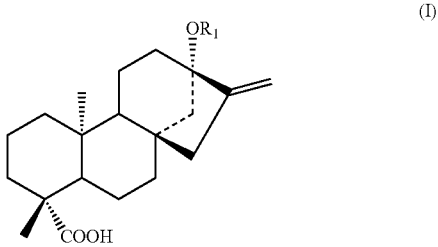

wherein $R_1$ represents H, a $C_1$-$C_{20}$ alkyl, a $C_2$-$C_{20}$ alkenyl, a $C_2$-$C_{20}$ alkynyl, a $C_4$-$C_{20}$ alkyldienyl, a $C_6$-$C_{18}$ aryl, a $C_6$-$C_{20}$ alkylaryl, a $C_6$-$C_{20}$ arylalkyl, a $C_4$-$C_{20}$ cycloalkyl, a $C_4$-$C_{20}$ cycloalkenyl, a ($C_3$-$C_{10}$ cycloalkyl) $C_1$-$C_{10}$ alkyl, or a sugar residue.

6. A method for producing a steviol glycoside, comprising:
   contacting, outside of a *stevia* plant, a protein consisting of the amino acid sequence of SEQ ID NO: 2 with a UDP-sugar and a compound represented by formula (I):

(I)

wherein $R_1$ represents H, a $C_1$-$C_{20}$ alkyl, a $C_2$-$C_{20}$ alkenyl, a $C_2$-$C_{20}$ alkynyl, a $C_4$-$C_{20}$ alkyldienyl, a $C_6$-$C_{18}$ aryl, a $C_6$-$C_{20}$ alkylaryl, a $C_6$-$C_{20}$ arylalkyl, a $C_4$-$C_{20}$ cycloalkyl, a $C_4$-$C_{20}$ cycloalkenyl, a ($C_3$-$C_{10}$ cycloalkyl) $C_1$-$C_{10}$ alkyl, or a sugar residue.

7. The method according to claim 6, wherein the sugar in the UDP-sugar is a hexose.

8. The method according to claim 6, wherein the sugar in the UDP-sugar is selected from glucose, mannose, and galactose.

9. The method according to claim 6, wherein $R_1$ is H or the sugar residue that is a glucose monomer, a glucose dimer, or a glucose trimer.

10. The method according to claim 6, wherein the compound is steviol, steviolmonoside, or steviolbioside.

11. The method according to claim 6, wherein the sugar in the UDP-sugar is glucose.

12. The method according to claim 6, wherein the steviol glycoside is steviolbioside, stevioside, rebaudioside A, rebaudioside B, rebaudioside C, rebaudioside D, rebaudioside E, rebaudioside F, or any combination thereof.

13. The non-human transformant according to claim 2, wherein the polynucleotide is inserted into an expression vector.

14. A method for producing an extract of the non-human transformant according to claim 2 or an extract of a culture of the non-human transformant according to claim 2, the method comprising:
   providing the transformant according to claim 2 or the culture of the transformant, and
   obtaining an extract of the transformant or of the culture of the transformant.

15. A method for producing a food, a pharmaceutical preparation, or an industrial raw material, the method comprising:
provide an extract of the transformant according to claim 2 or of a culture of the transformant,
adding the extract to a raw material of a food, a pharmaceutical preparation, or an industrial raw material, and
preparing the food, the pharmaceutical preparation, or the industrial raw material.

16. The method according to claim 15, wherein the food is selected from fermented foods, fruit drinks, soft drinks, sports drinks, tea, bakery products, noodles, pastas, cooked rice, sweets, bean curd, ham, bacon, sausage, fish cake (kamaboko), deep-fried fish cake (ageten), and puffy fish cake (hanpen).

17. The method according to claim 16, wherein the fermented foods are alcoholic beverages, tea, medicinal liquor, sweet cooking sherry (mirin), vinegar, soy sauce, miso (bean paste), and yogurt.

18. The method according to claim 15, wherein the pharmaceutical preparation is selected from cream, gel, lipstick, facial pack, ointment, dentifrice, and cleansing foam.

\* \* \* \* \*

SEQUENCE LISTING

<160> NUMBER OF SEQ ID NOS: 6

<210> SEQ ID NO 1
<211> LENGTH: 1446
<212> TYPE: DNA
<213> ORGANISM: Stevia rebaudiana
<220> FEATURE:
<221> NAME/KEY: CDS
<222> LOCATION: (1)..(1443)

<400> SEQUENCE: 1

| | | | | | | | | | | | | | | | | |
|---|---|---|---|---|---|---|---|---|---|---|---|---|---|---|---|---|
| atg | gat | gca | atg | gct | aca | act | gag | aag | aaa | cca | cac | gtc | atc | ttc | ata | 48 |
| Met | Asp | Ala | Met | Ala | Thr | Thr | Glu | Lys | Lys | Pro | His | Val | Ile | Phe | Ile | |
| 1 | | | | 5 | | | | | 10 | | | | | 15 | | |
| cca | ttt | cca | gca | caa | agc | cac | att | aaa | gcc | atg | ctc | aaa | cta | gca | caa | 96 |
| Pro | Phe | Pro | Ala | Gln | Ser | His | Ile | Lys | Ala | Met | Leu | Lys | Leu | Ala | Gln | |
| | | | 20 | | | | | 25 | | | | | 30 | | | |
| ctt | ctc | cac | cac | aaa | gga | ctc | cag | ata | acc | ttc | gtc | aac | acc | gac | ttc | 144 |
| Leu | Leu | His | His | Lys | Gly | Leu | Gln | Ile | Thr | Phe | Val | Asn | Thr | Asp | Phe | |
| | | | 35 | | | | | 40 | | | | | 45 | | | |
| atc | cac | aac | cag | ttt | ctt | gaa | tca | tcg | ggc | cca | cat | tgt | cta | gac | ggt | 192 |
| Ile | His | Asn | Gln | Phe | Leu | Glu | Ser | Ser | Gly | Pro | His | Cys | Leu | Asp | Gly | |
| | | | 50 | | | | | 55 | | | | | 60 | | | |
| tca | ccg | ggt | ttc | cgg | ttc | caa | acc | att | ccg | gat | ggt | gtt | tct | cac | agt | 240 |
| Ser | Pro | Gly | Phe | Arg | Phe | Gln | Thr | Ile | Pro | Asp | Gly | Val | Ser | His | Ser | |
| 65 | | | | | 70 | | | | | 75 | | | | | 80 | |
| ccg | gaa | gcg | agc | atc | cca | atc | aga | gaa | tca | ctc | ttg | aga | tcc | att | gaa | 288 |
| Pro | Glu | Ala | Ser | Ile | Pro | Ile | Arg | Glu | Ser | Leu | Leu | Arg | Ser | Ile | Glu | |
| | | | | 85 | | | | | 90 | | | | | 95 | | |
| acc | aac | ttc | ttg | gat | cgt | ttc | att | gat | ctt | gta | acc | aaa | ctt | ccg | gat | 336 |
| Thr | Asn | Phe | Leu | Asp | Arg | Phe | Ile | Asp | Leu | Val | Thr | Lys | Leu | Pro | Asp | |
| | | | 100 | | | | | 105 | | | | | 110 | | | |
| cct | ccg | act | tgt | att | atc | tca | gat | ggg | ttc | ttg | tcg | gtt | ttc | aca | att | 384 |
| Pro | Pro | Thr | Cys | Ile | Ile | Ser | Asp | Gly | Phe | Leu | Ser | Val | Phe | Thr | Ile | |
| | | | 115 | | | | | 120 | | | | | 125 | | | |
| gac | gct | gca | aaa | aag | ctt | gga | att | ccg | gtc | atg | atg | tat | tgg | aca | ctt | 432 |
| Asp | Ala | Ala | Lys | Lys | Leu | Gly | Ile | Pro | Val | Met | Met | Tyr | Trp | Thr | Leu | |
| | | | 130 | | | | | 135 | | | | | 140 | | | |
| gct | gcc | tgt | ggg | ttc | atg | ggt | ttt | tac | cat | att | cat | tct | ctc | att | gag | 480 |
| Ala | Ala | Cys | Gly | Phe | Met | Gly | Phe | Tyr | His | Ile | His | Ser | Leu | Ile | Glu | |
| 145 | | | | | 150 | | | | | 155 | | | | | 160 | |
| aaa | gga | ttt | gca | cca | ctt | aaa | gat | gca | agt | tac | ttg | aca | aat | ggg | tat | 528 |
| Lys | Gly | Phe | Ala | Pro | Leu | Lys | Asp | Ala | Ser | Tyr | Leu | Thr | Asn | Gly | Tyr | |
| | | | | 165 | | | | | 170 | | | | | 175 | | |
| ttg | gac | acc | gtc | att | gat | tgg | gtt | ccg | gga | atg | gaa | ggc | atc | cgt | ctc | 576 |
| Leu | Asp | Thr | Val | Ile | Asp | Trp | Val | Pro | Gly | Met | Glu | Gly | Ile | Arg | Leu | |
| | | | 180 | | | | | 185 | | | | | 190 | | | |
| aag | gat | ttc | ccg | ctg | gac | tgg | agc | act | gac | ctc | aat | gac | aaa | gtt | ttg | 624 |
| Lys | Asp | Phe | Pro | Leu | Asp | Trp | Ser | Thr | Asp | Leu | Asn | Asp | Lys | Val | Leu | |
| | | | 195 | | | | | 200 | | | | | 205 | | | |
| atg | ttc | act | acg | gaa | gct | cct | caa | agg | tca | cac | acg | gtt | tca | cat | cat | 672 |
| Met | Phe | Thr | Thr | Glu | Ala | Pro | Gln | Arg | Ser | His | Thr | Val | Ser | His | His | |
| | | | 210 | | | | | 215 | | | | | 220 | | | |
| att | ttc | cac | acg | ttc | gat | gag | ttg | gag | cct | agt | att | ata | aaa | act | ttg | 720 |
| Ile | Phe | His | Thr | Phe | Asp | Glu | Leu | Glu | Pro | Ser | Ile | Ile | Lys | Thr | Leu | |
| 225 | | | | | 230 | | | | | 235 | | | | | 240 | |
| tca | ttg | agg | tat | aat | cac | att | tac | acc | atc | ggc | cca | ctg | caa | tta | ctt | 768 |
| Ser | Leu | Arg | Tyr | Asn | His | Ile | Tyr | Thr | Ile | Gly | Pro | Leu | Gln | Leu | Leu | |
| | | | | 245 | | | | | 250 | | | | | 255 | | |
| ctt | gat | caa | ata | ccc | gaa | gag | aaa | aag | caa | act | gga | att | acg | agt | ctc | 816 |
| Leu | Asp | Gln | Ile | Pro | Glu | Glu | Lys | Lys | Gln | Thr | Gly | Ile | Thr | Ser | Leu | |

```
cat gga tac agt tta gta aaa gaa gaa cca gag tgt ttc cag tgg ctt    864
His Gly Tyr Ser Leu Val Lys Glu Glu Pro Glu Cys Phe Gln Trp Leu
            275                 280                 285 cag tct aaa gaa cca aat tcc gtc gtt tat gta aat ttt gga agt act    912
Gln Ser Lys Glu Pro Asn Ser Val Val Tyr Val Asn Phe Gly Ser Thr
        290                 295                 300 aca gta atg tct tta gaa gac atg acg gaa ttt ggt tgg gga ctt gct    960
Thr Val Met Ser Leu Glu Asp Met Thr Glu Phe Gly Trp Gly Leu Ala
305                 310                 315                 320 aat agc aac cat tat ttc ctt tgg atc atc cga tca aac ttg gtg ata   1008
Asn Ser Asn His Tyr Phe Leu Trp Ile Ile Arg Ser Asn Leu Val Ile
            325                 330                 335 ggg gaa aat gca gtt ttg ccc cct gaa ctt gag gaa cat ata aag aaa   1056
Gly Glu Asn Ala Val Leu Pro Pro Glu Leu Glu Glu His Ile Lys Lys
        340                 345                 350 aga ggc ttt att gct agc tgg tgt tca caa gaa aag gtc ttg aag cac   1104
Arg Gly Phe Ile Ala Ser Trp Cys Ser Gln Glu Lys Val Leu Lys His
                355                 360                 365 cct tcg gtt gga ggg ttc ttg act cat tgt ggg tgg gga tcg acc atc   1152
Pro Ser Val Gly Gly Phe Leu Thr His Cys Gly Trp Gly Ser Thr Ile
370                 375                 380 gag agc ttg tct gct ggg gtg cca atg ata tgc tgg cct tat tcg tgg   1200
Glu Ser Leu Ser Ala Gly Val Pro Met Ile Cys Trp Pro Tyr Ser Trp
385                 390                 395                 400 gac cag ctg acc aac tgt agg tat ata tgc aaa gaa tgg gag gtt ggg   1248
Asp Gln Leu Thr Asn Cys Arg Tyr Ile Cys Lys Glu Trp Glu Val Gly
            405                 410                 415 ctc gag atg gga acc aaa gtg aaa cga gat gaa gtc aag agg ctt gta   1296
Leu Glu Met Gly Thr Lys Val Lys Arg Asp Glu Val Lys Arg Leu Val
        420                 425                 430 caa gag ttg atg gga gaa gga ggt cac aaa atg agg aac aag gct aaa   1344
Gln Glu Leu Met Gly Glu Gly Gly His Lys Met Arg Asn Lys Ala Lys
                435                 440                 445 gat tgg aaa gaa aag gct cgc att gca ata gct cct aac ggt tca tct   1392
Asp Trp Lys Glu Lys Ala Arg Ile Ala Ile Ala Pro Asn Gly Ser Ser
450                 455                 460 tct ttg aac ata gac aaa atg gtc aag gaa atc acc gtg cta gca aga   1440
Ser Leu Asn Ile Asp Lys Met Val Lys Glu Ile Thr Val Leu Ala Arg
465                 470                 475                 480 aac tag                                                           1446
Asn

<210> SEQ ID NO 2
<211> LENGTH: 481
<212> TYPE: PRT
<213> ORGANISM: Stevia rebaudiana

<400> SEQUENCE: 2

Met Asp Ala Met Ala Thr Thr Glu Lys Lys Pro His Val Ile Phe Ile
1               5                   10                  15

Pro Phe Pro Ala Gln Ser His Ile Lys Ala Met Leu Lys Leu Ala Gln
            20                  25                  30

Leu Leu His His Lys Gly Leu Gln Ile Thr Phe Val Asn Thr Asp Phe
        35                  40                  45

Ile His Asn Gln Phe Leu Glu Ser Ser Gly Pro His Cys Leu Asp Gly
    50                  55                  60

Ser Pro Gly Phe Arg Phe Gln Thr Ile Pro Asp Gly Val Ser His Ser
65                  70                  75                  80
```

-continued

```
Pro Glu Ala Ser Ile Pro Ile Arg Glu Ser Leu Leu Arg Ser Ile Glu
                85                  90                  95

Thr Asn Phe Leu Asp Arg Phe Ile Asp Leu Val Thr Lys Leu Pro Asp
            100                 105                 110

Pro Pro Thr Cys Ile Ile Ser Asp Gly Phe Leu Ser Val Phe Thr Ile
            115                 120                 125

Asp Ala Ala Lys Lys Leu Gly Ile Pro Val Met Met Tyr Trp Thr Leu
130                 135                 140

Ala Ala Cys Gly Phe Met Gly Phe Tyr His Ile His Ser Leu Ile Glu
145                 150                 155                 160

Lys Gly Phe Ala Pro Leu Lys Asp Ala Ser Tyr Leu Thr Asn Gly Tyr
                165                 170                 175

Leu Asp Thr Val Ile Asp Trp Val Pro Gly Met Glu Gly Ile Arg Leu
            180                 185                 190

Lys Asp Phe Pro Leu Asp Trp Ser Thr Asp Leu Asn Asp Lys Val Leu
            195                 200                 205

Met Phe Thr Thr Glu Ala Pro Gln Arg Ser His Thr Val Ser His His
            210                 215                 220

Ile Phe His Thr Phe Asp Glu Leu Glu Pro Ser Ile Ile Lys Thr Leu
225                 230                 235                 240

Ser Leu Arg Tyr Asn His Ile Tyr Thr Ile Gly Pro Leu Gln Leu Leu
                245                 250                 255

Leu Asp Gln Ile Pro Glu Glu Lys Lys Gln Thr Gly Ile Thr Ser Leu
            260                 265                 270

His Gly Tyr Ser Leu Val Lys Glu Glu Pro Glu Cys Phe Gln Trp Leu
            275                 280                 285

Gln Ser Lys Glu Pro Asn Ser Val Val Tyr Val Asn Phe Gly Ser Thr
290                 295                 300

Thr Val Met Ser Leu Glu Asp Met Thr Glu Phe Gly Trp Gly Leu Ala
305                 310                 315                 320

Asn Ser Asn His Tyr Phe Leu Trp Ile Ile Arg Ser Asn Leu Val Ile
                325                 330                 335

Gly Glu Asn Ala Val Leu Pro Pro Glu Leu Glu His Ile Lys Lys
            340                 345                 350

Arg Gly Phe Ile Ala Ser Trp Cys Ser Gln Glu Lys Val Leu Lys His
            355                 360                 365

Pro Ser Val Gly Gly Phe Leu Thr His Cys Gly Trp Gly Ser Thr Ile
370                 375                 380

Glu Ser Leu Ser Ala Gly Val Pro Met Ile Cys Trp Pro Tyr Ser Trp
385                 390                 395                 400

Asp Gln Leu Thr Asn Cys Arg Tyr Ile Cys Lys Glu Trp Glu Val Gly
                405                 410                 415

Leu Glu Met Gly Thr Lys Val Lys Arg Asp Glu Val Lys Arg Leu Val
            420                 425                 430

Gln Glu Leu Met Gly Glu Gly His Lys Met Arg Asn Lys Ala Lys
            435                 440                 445

Asp Trp Lys Glu Lys Ala Arg Ile Ala Ile Ala Pro Asn Gly Ser Ser
450                 455                 460

Ser Leu Asn Ile Asp Lys Met Val Lys Glu Ile Thr Val Leu Ala Arg
465                 470                 475                 480

Asn
```

-continued

```
<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cacccatatg gatgcaatgg ctacaactga gaa                                      33

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agatctctag tttcttgcta gcacggtgat tt                                       32

<210> SEQ ID NO 5
<211> LENGTH: 1458
<212> TYPE: DNA
<213> ORGANISM: Stevia rebaudiana
<220> FEATURE:
<221> NAME/KEY: CDS
<222> LOCATION: (1)..(1455)

<400> SEQUENCE: 5 atg tac aac gtt act tat cat caa aat tca aaa gca atg gct acc agt          48
Met Tyr Asn Val Thr Tyr His Gln Asn Ser Lys Ala Met Ala Thr Ser
1               5                   10                  15 gac tcc ata gtt gac gac cgt aag cag ctt cat gtt gcg acg ttc cca          96
Asp Ser Ile Val Asp Asp Arg Lys Gln Leu His Val Ala Thr Phe Pro
                20                  25                  30 tgg ctt gct ttc ggt cac atc ctc cct tac ctt cag ctt tcg aaa ttg         144
Trp Leu Ala Phe Gly His Ile Leu Pro Tyr Leu Gln Leu Ser Lys Leu
            35                  40                  45 ata gct gaa aag ggt cac aaa gtc tcg ttt ctt tct acc acc aga aac         192
Ile Ala Glu Lys Gly His Lys Val Ser Phe Leu Ser Thr Thr Arg Asn
        50                  55                  60 att caa cgt ctc tct tct cat atc tcg cca ctc ata aat gtt gtt caa         240
Ile Gln Arg Leu Ser Ser His Ile Ser Pro Leu Ile Asn Val Val Gln
65                  70                  75                  80 ctc aca ctt cca cgt gtc caa gag ctg ccg gag gat gca gag gcg acc         288
Leu Thr Leu Pro Arg Val Gln Glu Leu Pro Glu Asp Ala Glu Ala Thr
                85                  90                  95 act gac gtc cac cct gaa gat att cca tat ctc aag aag gct tct gat         336
Thr Asp Val His Pro Glu Asp Ile Pro Tyr Leu Lys Lys Ala Ser Asp
                100                 105                 110 ggt ctt caa ccg gag gtc acc cgg ttt cta gaa caa cac tct ccg gac         384
Gly Leu Gln Pro Glu Val Thr Arg Phe Leu Glu Gln His Ser Pro Asp
            115                 120                 125 tgg att att tat gat tat act cac tac tgg ttg cca tcc atc gcg gct         432
Trp Ile Ile Tyr Asp Tyr Thr His Tyr Trp Leu Pro Ser Ile Ala Ala
        130                 135                 140 agc ctc ggt atc tca cga gcc cac ttc tcc gtc acc act cca tgg gcc         480
Ser Leu Gly Ile Ser Arg Ala His Phe Ser Val Thr Thr Pro Trp Ala
145                 150                 155                 160 att gct tat atg gga ccc tca gct gac gcc atg ata aat ggt tca gat         528
Ile Ala Tyr Met Gly Pro Ser Ala Asp Ala Met Ile Asn Gly Ser Asp
                165                 170                 175
```

-continued

| | |
|---|---|
| ggt cga acc acg gtt gag gat ctc acg aca ccg ccc aag tgg ttt ccc<br>Gly Arg Thr Thr Val Glu Asp Leu Thr Thr Pro Pro Lys Trp Phe Pro<br>                  180                      185                  190 | 576 |
| ttt ccg acc aaa gta tgc tgg cgg aag cat gat ctt gcc cga ctg gtg<br>Phe Pro Thr Lys Val Cys Trp Arg Lys His Asp Leu Ala Arg Leu Val<br>              195                      200                  205 | 624 |
| cct tac aaa gct ccg ggg ata tct gat gga tac cgt atg ggg ctg gtt<br>Pro Tyr Lys Ala Pro Gly Ile Ser Asp Gly Tyr Arg Met Gly Leu Val<br>210                      215                      220 | 672 |
| ctt aag gga tct gat tgt ttg ctt tcc aaa tgt tac cat gag ttt gga<br>Leu Lys Gly Ser Asp Cys Leu Leu Ser Lys Cys Tyr His Glu Phe Gly<br>225                    230                      235                  240 | 720 |
| act caa tgg cta cct ctt ttg gag aca cta cac caa gta ccg gtg gtt<br>Thr Gln Trp Leu Pro Leu Leu Glu Thr Leu His Gln Val Pro Val Val<br>                  245                      250                  255 | 768 |
| ccg gtg gga tta ctg cca ccg gaa ata ccc gga gac gag aaa gat gaa<br>Pro Val Gly Leu Leu Pro Pro Glu Ile Pro Gly Asp Glu Lys Asp Glu<br>                      260                      265                  270 | 816 |
| aca tgg gtg tca atc aag aaa tgg ctc gat ggt aaa caa aaa ggc agt<br>Thr Trp Val Ser Ile Lys Lys Trp Leu Asp Gly Lys Gln Lys Gly Ser<br>              275                      280                  285 | 864 |
| gtg gtg tac gtt gca tta gga agc gag gtt ttg gtg agc caa acc gag<br>Val Val Tyr Val Ala Leu Gly Ser Glu Val Leu Val Ser Gln Thr Glu<br>                  290                      295                  300 | 912 |
| gtt gtt gag tta gca ttg ggt ctc gag ctt tct ggg ttg cca ttt gtt<br>Val Val Glu Leu Ala Leu Gly Leu Glu Leu Ser Gly Leu Pro Phe Val<br>305                      310                      315                  320 | 960 |
| tgg gct tat aga aaa cca aaa ggt ccc gcg aag tca gac tcg gtg gag<br>Trp Ala Tyr Arg Lys Pro Lys Gly Pro Ala Lys Ser Asp Ser Val Glu<br>                      325                      330                  335 | 1008 |
| ttg cca gac ggg ttc gtg gaa cga act cgt gac cgt ggg ttg gtc tgg<br>Leu Pro Asp Gly Phe Val Glu Arg Thr Arg Asp Arg Gly Leu Val Trp<br>                  340                      345                  350 | 1056 |
| acg agt tgg gca cct cag tta cga ata ctg agc cat gag tcg gtt tgt<br>Thr Ser Trp Ala Pro Gln Leu Arg Ile Leu Ser His Glu Ser Val Cys<br>              355                      360                  365 | 1104 |
| ggt ttc ttg act cat tgt ggt tct gga tca att gtg gaa ggg cta atg<br>Gly Phe Leu Thr His Cys Gly Ser Gly Ser Ile Val Glu Gly Leu Met<br>370                      375                      380 | 1152 |
| ttt ggt cac cct cta atc atg cta ccg att ttt ggg gac caa cct ctg<br>Phe Gly His Pro Leu Ile Met Leu Pro Ile Phe Gly Asp Gln Pro Leu<br>385                      390                      395                  400 | 1200 |
| aat gct cga tta ctg gag gac aaa cag gtg gga atc gag ata cca aga<br>Asn Ala Arg Leu Leu Glu Asp Lys Gln Val Gly Ile Glu Ile Pro Arg<br>                      405                      410                  415 | 1248 |
| aat gag gaa gat ggt tgc ttg acc aag gag tcg gtt gct aga tca ctg<br>Asn Glu Glu Asp Gly Cys Leu Thr Lys Glu Ser Val Ala Arg Ser Leu<br>                  420                      425                  430 | 1296 |
| agg tcc gtt gtt gtg gaa aaa gaa ggg gag atc tac aag gcg aac gcg<br>Arg Ser Val Val Val Glu Lys Glu Gly Glu Ile Tyr Lys Ala Asn Ala<br>              435                      440                  445 | 1344 |
| agg gag ctg agt aaa atc tat aac gac act aag gtt gaa aaa gaa tat<br>Arg Glu Leu Ser Lys Ile Tyr Asn Asp Thr Lys Val Glu Lys Glu Tyr<br>450                      455                      460 | 1392 |
| gta agc caa ttc gta gac tat ttg gaa aag aat gcg cgt gcg gtt gcc<br>Val Ser Gln Phe Val Asp Tyr Leu Glu Lys Asn Ala Arg Ala Val Ala<br>465                      470                      475                  480 | 1440 |
| atc gat cat gag agt taa<br>Ile Asp His Glu Ser | 1458 |

-continued

485

<210> SEQ ID NO 6
<211> LENGTH: 485
<212> TYPE: PRT
<213> ORGANISM: Stevia rebaudiana

<400> SEQUENCE: 6

Met Tyr Asn Val Thr Tyr His Gln Asn Ser Lys Ala Met Ala Thr Ser
1               5                   10                  15

Asp Ser Ile Val Asp Asp Arg Lys Gln Leu His Val Ala Thr Phe Pro
            20                  25                  30

Trp Leu Ala Phe Gly His Ile Leu Pro Tyr Leu Gln Leu Ser Lys Leu
        35                  40                  45

Ile Ala Glu Lys Gly His Lys Val Ser Phe Leu Ser Thr Thr Arg Asn
    50                  55                  60

Ile Gln Arg Leu Ser Ser His Ile Ser Pro Leu Ile Asn Val Val Gln
65                  70                  75                  80

Leu Thr Leu Pro Arg Val Gln Glu Leu Pro Glu Asp Ala Glu Ala Thr
                85                  90                  95

Thr Asp Val His Pro Glu Asp Ile Pro Tyr Leu Lys Lys Ala Ser Asp
            100                 105                 110

Gly Leu Gln Pro Glu Val Thr Arg Phe Leu Glu Gln His Ser Pro Asp
        115                 120                 125

Trp Ile Ile Tyr Asp Tyr Thr His Tyr Trp Leu Pro Ser Ile Ala Ala
    130                 135                 140

Ser Leu Gly Ile Ser Arg Ala His Phe Ser Val Thr Thr Pro Trp Ala
145                 150                 155                 160

Ile Ala Tyr Met Gly Pro Ser Ala Asp Ala Met Ile Asn Gly Ser Asp
                165                 170                 175

Gly Arg Thr Thr Val Glu Asp Leu Thr Thr Pro Pro Lys Trp Phe Pro
            180                 185                 190

Phe Pro Thr Lys Val Cys Trp Arg Lys His Asp Leu Ala Arg Leu Val
        195                 200                 205

Pro Tyr Lys Ala Pro Gly Ile Ser Asp Gly Tyr Arg Met Gly Leu Val
    210                 215                 220

Leu Lys Gly Ser Asp Cys Leu Leu Ser Lys Cys Tyr His Glu Phe Gly
225                 230                 235                 240

Thr Gln Trp Leu Pro Leu Leu Glu Thr Leu His Gln Val Pro Val Val
                245                 250                 255

Pro Val Gly Leu Leu Pro Pro Glu Ile Pro Gly Asp Glu Lys Asp Glu
            260                 265                 270

Thr Trp Val Ser Ile Lys Lys Trp Leu Asp Gly Lys Gln Lys Gly Ser
        275                 280                 285

Val Val Tyr Val Ala Leu Gly Ser Glu Val Leu Val Ser Gln Thr Glu
    290                 295                 300

Val Val Glu Leu Ala Leu Gly Leu Glu Leu Ser Gly Leu Pro Phe Val
305                 310                 315                 320

Trp Ala Tyr Arg Lys Pro Lys Gly Pro Ala Lys Ser Asp Ser Val Glu
                325                 330                 335

Leu Pro Asp Gly Phe Val Glu Arg Thr Arg Asp Arg Gly Leu Val Trp
            340                 345                 350

Thr Ser Trp Ala Pro Gln Leu Arg Ile Leu Ser His Glu Ser Val Cys
        355                 360                 365

```
Gly Phe Leu Thr His Cys Gly Ser Gly Ser Ile Val Glu Gly Leu Met
    370             375                 380
Phe Gly His Pro Leu Ile Met Leu Pro Ile Phe Gly Asp Gln Pro Leu
385             390                 395                 400
Asn Ala Arg Leu Leu Glu Asp Lys Gln Val Gly Ile Glu Ile Pro Arg
            405                 410                 415
Asn Glu Glu Asp Gly Cys Leu Thr Lys Glu Ser Val Ala Arg Ser Leu
            420                 425                 430
Arg Ser Val Val Glu Lys Glu Gly Glu Ile Tyr Lys Ala Asn Ala
        435                 440                 445
Arg Glu Leu Ser Lys Ile Tyr Asn Asp Thr Lys Val Glu Lys Glu Tyr
450                 455                 460
Val Ser Gln Phe Val Asp Tyr Leu Glu Lys Asn Ala Arg Ala Val Ala
465             470                 475                 480
Ile Asp His Glu Ser
            485
```